(12) United States Patent
Cow et al.

(10) Patent No.: US 7,750,032 B2
(45) Date of Patent: Jul. 6, 2010

(54) COMPOUNDS AND COMPOSITIONS AS PPAR MODULATORS

(75) Inventors: Christopher Cow, San Diego, CA (US);
Robert Epple, San Diego, CA (US);
Xing Wang, San Diego, CA (US);
Yongping Xie, San Diego, CA (US);
Hans Martin Seidel, Del Mar, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 11/815,096

(22) PCT Filed: Feb. 3, 2006

(86) PCT No.: PCT/US2006/003924

§ 371 (c)(1),
(2), (4) Date: Jan. 8, 2009

(87) PCT Pub. No.: WO2006/084176

PCT Pub. Date: Aug. 10, 2006

(65) Prior Publication Data

US 2009/0137591 A1    May 28, 2009

Related U.S. Application Data

(60) Provisional application No. 60/649,962, filed on Feb. 3, 2005.

(51) Int. Cl.
| | |
|---|---|
| C07D 213/64 | (2006.01) |
| C07D 265/30 | (2006.01) |
| C07D 233/64 | (2006.01) |
| C07D 231/12 | (2006.01) |
| C07D 413/10 | (2006.01) |
| C07D 401/04 | (2006.01) |
| A61K 31/4155 | (2006.01) |
| A61K 31/4178 | (2006.01) |
| A61K 31/4164 | (2006.01) |
| A61K 31/4439 | (2006.01) |
| A61K 31/5377 | (2006.01) |

(52) U.S. Cl. ............... 514/400; 514/238.5; 514/236.5; 514/341; 514/406; 548/342.5; 548/376.1; 546/274.1; 546/275.4; 544/139

(58) Field of Classification Search ............... 548/268.2
See application file for complete search history.

(56) References Cited

U.S. PATENT DOCUMENTS

| 6,613,789 B2 * | 9/2003 | Khanna et al. ............... 514/397 |
| 2007/0112045 A1 * | 5/2007 | Mantlo et al. ................ 514/362 |

OTHER PUBLICATIONS

Jordan, V. C. Nature Reviews: Drug Discovery, 2, 2003, pp. 205-213.*
Golub et al., Science, vol. 286, Oct. 15, 1999, pp. 531-537.*
Hussain et al. Diabetes Research and Clinical Practice 2007, 76, 317-326.*

* cited by examiner

*Primary Examiner*—Rebecca L Anderson
*Assistant Examiner*—Matthew P Coughlin
(74) *Attorney, Agent, or Firm*—Scott W. Reid; D. Phil; Genomics Institute of the Novartis Research Foundation

(57) ABSTRACT

The invention provides trisubstituted pyrazoles and imidazoles of Formula I:

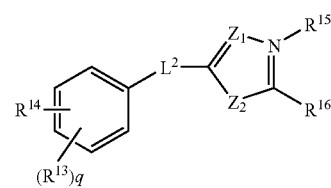

wherein $L^2$, $q$, $R^{13}$, $R^{14}$, $R^{15}$, $R^{16}$, $Z_1$ and $Z_2$ are as described in the Summary of the Invention; and methods of using such compounds to treat or prevent diseases or disorders associated with the activity of the peroxisome proliferator-activated receptor (PPAR) families, particularly the activity of PPARδ.

9 Claims, No Drawings

COMPOUNDS AND COMPOSITIONS AS PPAR MODULATORS

CROSS-REFERENCE TO RELATED APPLICATIONS

This application is a 371 U.S. national phase application of international application number PCT/US2006/003924 filed 3 Feb. 2006, which application claims priority to U.S. Provisional Patent Application No. 60/649,962, filed 3 Feb. 2005. The full disclosures of these applications are incorporated herein by reference in their entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of the Peroxisome Proliferator-Activated Receptor (PPAR) families, particularly the activity of PPARδ.

2. Background

Peroxisome Proliferator Activated Receptors (PPARs) are members of the nuclear hormone receptor super family, which are ligand-activated transcription factors regulating gene expression. Certain PPARs are associated with a number of disease states including dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease. Accordingly, molecules that modulate the activity of PPARs, particularly PPARδ, are useful as therapeutic agents in the treatment of such diseases.

SUMMARY OF THE INVENTION

In one aspect, the present invention provides a compound of Formula I:

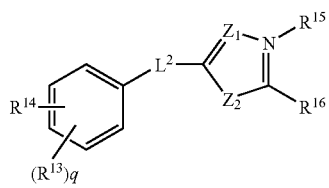

in which:

q is an integer selected from 0 to 3;

$Z_1$ and $Z_2$ are independently selected from CH and N;

$L^2$ is selected from —XOX—, —XS(O)$_{0-2}$X— and —XS(O)$_{0-2}$XO—; wherein X is independently selected from a bond and $C_{1-4}$alkylene; wherein any alkylene of $L^2$ can be optionally substituted by 1 to 3 radicals selected from halo, $C_{1-6}$alkyl, $C_{1-6}$alkoxy, halo-substituted-$C_{1-6}$alkyl and halo-substituted-$C_{1-6}$alkoxy;

$R^{13}$ is selected from halo, $C_{1-6}$alkyl, $C_{1-6}$alkoxy, hydroxy-$C_{1-6}$alkyl, halo-substituted-$C_{1-6}$alkyl, halo-substituted-$C_{1-6}$alkoxy, $C_{6-10}$aryl, $C_{5-10}$heteroaryl, $C_{3-12}$cycloalkyl and $C_{3-8}$heterocycloalkyl; wherein any aryl, heteroaryl, cycloalkyl and heterocycloalkyl of $R^{13}$ is optionally substituted with 1 to 3 radicals independently selected from halo, nitro, cyano, $C_{1-6}$alkyl, $C_{1-6}$alkoxy, hydroxy-$C_{1-6}$alkyl, halo-substituted-$C_{1-6}$alkyl and halo-substituted-$C_{1-6}$alkoxy;

$R^{14}$ is selected from —XOXC(O)OR$^{17}$ and —XC(O)OR$^{17}$; wherein X is a bond or $C_{1-4}$alkylene; and $R^{17}$ is selected from hydrogen and $C_{1-6}$alkyl;

$R^{15}$ and $R^{16}$ are independently selected from —R$^{18}$ and —YR$^{18}$; wherein Y is a selected from $C_{1-6}$alkylene, $C_{2-6}$alkenylene, $C_{2-6}$alkynylene, —C(O)NR$^{17}$— and —OX—; X is a bond or $C_{1-4}$alkylene; $R^{17}$ is selected from hydrogen and $C_{1-6}$alkyl; and $R^{18}$ is selected from $C_{3-12}$cycloalkyl, $C_{3-8}$heterocycloalkyl, $C_{6-10}$aryl and $C_{5-13}$heteroaryl; or $R^{15}$ and $R^{16}$ together with the atoms to which $R^{15}$ and $R^{16}$ are attached form fused bicyclic or tricyclic $C_{5-14}$heteroaryl;

wherein any aryl, heteroaryl, cycloalkyl and heterocycloalkyl of $R^{18}$, or the combination of $R^{15}$ and $R^{16}$, is optionally substituted with 1 to 3 radicals independently selected from halo, nitro, cyano, $C_{1-6}$alkyl, $C_{1-6}$alkoxy, $C_{1-6}$alkylthio, hydroxy-$C_{1-6}$alkyl, halo-substituted-$C_{1-6}$alkyl, halo-substituted-$C_{1-6}$alkoxy, $C_{3-12}$cycloalkyl, $C_{3-8}$heterocycloalkyl, $C_{6-10}$aryl, $C_{5-13}$heteroaryl, —XS(O)$_{0-2}$R$^{17}$, —XS(O)$_{0-2}$XR$^{19}$, —XNR$^{17}$R$^{17}$, —XNR$^{17}$S(O)$_{0-2}$R$^{17}$, —XNR$^{17}$C(O)R$^{17}$, —XC(O)NR$^{17}$R$^{17}$, —XNR$^{17}$C(O)R$^{19}$, —XC(O)NR$^{17}$R$^{19}$, —XC(O)R$^{19}$, —XNR$^{17}$XR$^{19}$ and —XOXR$^{19}$; wherein any aryl, heteroaryl, cycloalkyl or heterocycloalkyl substituent is further optionally substituted with 1 to 3 radicals independently selected from halo, nitro, cyano, $C_{1-6}$alkyl, $C_{1-6}$alkoxy, $C_{1-6}$alkylthio, hydroxy-$C_{1-6}$alkyl, halo-substituted-$C_{1-6}$alkyl and halo-substituted-$C_{1-6}$alkoxy; wherein X is a bond or $C_{1-4}$alkylene; $R^{17}$ is selected from hydrogen and $C_{1-6}$alkyl; and $R^{19}$ is selected from $C_{3-12}$cycloalkyl, $C_{3-8}$heterocycloalkyl, $C_{6-10}$aryl and $C_{5-10}$heteroaryl; wherein any aryl, heteroaryl, cycloalkyl or heterocycloalkyl of $R^{19}$ is optionally substituted with 1 to 3 radicals independently selected from halo, nitro, cyano, $C_{1-6}$alkyl, $C_{1-6}$alkoxy, halo-substituted-$C_{1-6}$alkyl and halo-substituted-$C_{1-6}$alkoxy;

and the N-oxide derivatives, prodrug derivatives, protected derivatives, individual isomers and mixture of isomers thereof; and the pharmaceutical acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of PPAR activity, particularly PPARδ, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which PPAR activity, particularly PPARδ, activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. "$C_{6-10}$aryl$C_{0-4}$alkyl" means an aryl as described above connected via a alkylene grouping. For example, $C_{6-10}$aryl-$C_{0-4}$alkyl includes phenethyl, benzyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of PPARδ activity can prevent, inhibit or ameliorate the pathology and/or symptomology of the diseases, which method comprises administering to the animal a therapeutically effective amount of a compound of Formula I.

In one embodiment, with reference to compounds of Formula I, q is an integer selected from 0 to 3; $L^2$ is selected from —XOX—, —XS(O)$_{0-2}$X— and —XS(O)$_{0-2}$XO—; wherein X is independently selected from a bond and $C_{1-4}$alkylene; wherein any alkylene of $L^2$ can be optionally substituted by 1 to 3 radicals selected from halo, $C_{1-6}$alkyl, $C_{1-6}$alkoxy, halo-substituted-$C_{1-6}$alkyl and halo-substituted-$C_{1-6}$alkoxy; $R^{13}$ is $C_{1-6}$alkyl, $C_{1-6}$alkoxy and halogen; $R^{14}$ is selected from —XOXC(O)OR$^{17}$ and —XC(O)OR$^{17}$; wherein X is a bond or $C_{1-4}$alkylene; and $R^{17}$ is selected from hydrogen and $C_{1-6}$alkyl; $R^{15}$ and $R^{16}$ are independently selected from —R$^{18}$ and —YR$^{18}$; wherein Y is a selected from $C_{1-6}$alkylene, $C_{2-6}$alkenylene, —C(O)NR$^{17}$— and —OX—; X is a bond or $C_{1-4}$alkylene; $R^{17}$ is selected from hydrogen and $C_{1-6}$alkyl; and $R^{18}$ is selected from $C_{6-10}$aryl, $C_{3-12}$cycloalkyl and $C_{5-13}$heteroaryl; or $R^{15}$ and $R^{16}$ together with the atoms to which $R^{15}$ and $R^{16}$ are attached form fused bicyclic or tricyclic $C_{5-14}$heteroaryl; wherein any aryl, heteroaryl and cycloalkyl of $R^{18}$, or the combination of $R^{15}$ and $R^{16}$, is optionally substituted with 1 to 3 radicals independently selected from halo, nitro, cyano, $C_{1-6}$alkyl, $C_{1-6}$alkoxy, $C_{1-6}$alkylthio, hydroxy-$C_{1-6}$alkyl, halo-substituted-$C_{1-6}$alkyl, halo-substituted-$C_{1-6}$alkoxy, $C_{3-12}$cycloalkyl, $C_{3-8}$heterocycloalkyl, $C_{6-10}$aryl optionally substituted with $C_{1-6}$alkoxy, $C_{5-13}$heteroaryl, —XS(O)$_{0-2}$R$^{17}$, —XS(O)$_{0-2}$XR$^{19}$, —XNR$^{17}$R$^{17}$, —XNR$^{17}$S(O)$_{0-2}$R$^{17}$, —XNR$^{17}$C(O)R$^{17}$, —XC(O)NR$^{17}$R$^{17}$, —XNR$^{17}$C(O)R$^{19}$, —XC(O)NR$^{17}$R$^{19}$, —XC(O)R$^{19}$, —XNR$^{17}$XR$^{19}$ and —XOXR$^{19}$; wherein X is a bond or $C_{1-4}$alkylene; $R^{17}$ is selected from hydrogen and $C_{1-6}$alkyl; and $R^{19}$ is selected from $C_{6-10}$aryl, $C_{5-10}$heteroaryl, $C_{3-8}$heterocycloalkyl and $C_{3-12}$ cycloalkyl; wherein any aryl, heteroaryl, cycloalkyl or heterocycloalkyl of $R^{19}$ is optionally substituted with 1 to 3 radicals independently selected from halo, nitro, cyano, $C_{1-6}$alkyl, $C_{1-6}$alkoxy, halo-substituted-$C_{1-6}$alkyl and halo-substituted-$C_{1-6}$alkoxy.

In another embodiment, compounds are selected from Formulae Ia, Ib, Ic and Id:

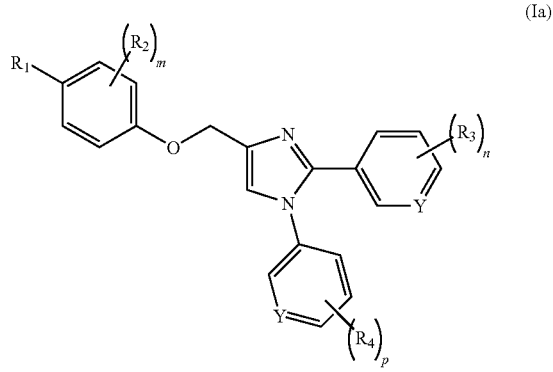

(Ia)

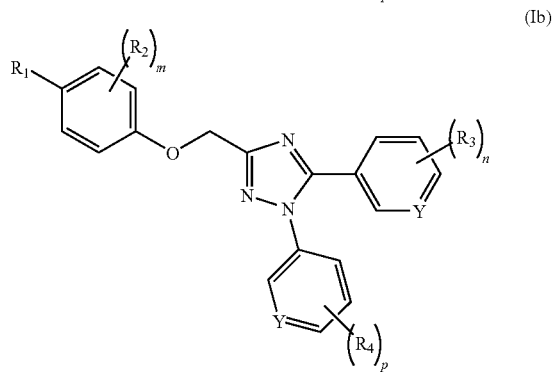

(Ib)

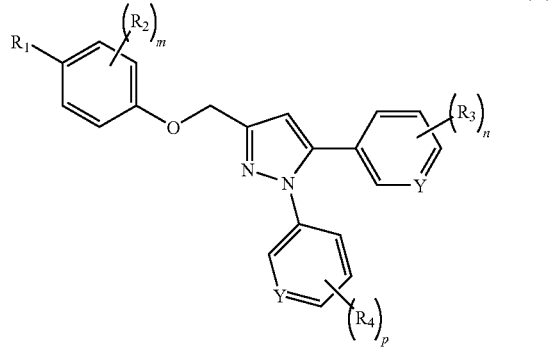

(Ic)

-continued

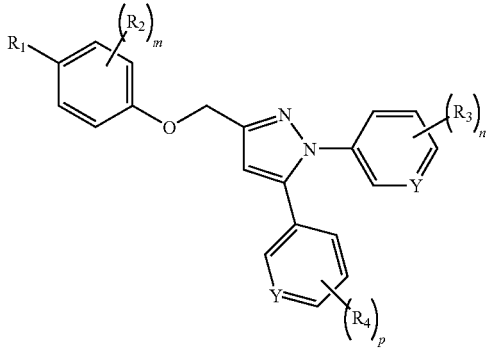

(Id)

in which: m, n and p are independently selected from 0, 1, 2 and 3; each Y is independently selected from CH and N; $R_1$ is selected from XOXC(O)OR$_5$ and XC(O)OR$_5$; wherein X is selected from a bond, $C_{1-6}$alkylene and $C_{2-6}$alkenylene; and $R_5$ is selected from hydrogen and $C_{1-6}$alkyl; $R_2$ is $C_{1-6}$alkyl; $R_3$ is selected from $C_{1-6}$alkoxy, $C_{1-6}$alkylthio, halo-substituted-$C_{1-6}$alkyl, halo-substituted-$C_{1-6}$alkoxy and halo-substituted-$C_{1-6}$alkylthio; and $R_4$ is selected from $C_{1-6}$alkoxy, $C_{1-6}$alkylthio, halo-substituted-$C_{1-6}$alkyl, halo-substituted-$C_{1-6}$alkoxy, halo-substituted-$C_{1-6}$alkylthio and $C_{3-8}$heterocycloalkyl.

In another embodiment, m, n and p are independently selected from 0, 1 and 2; Y is selected from CH and N; $R_1$ is XOXC(O)OR$_5$; wherein X is selected from a bond, $C_{1-6}$alkylene and $C_{2-6}$alkenylene; and $R_5$ is selected from hydrogen and $C_{1-6}$alkyl; $R_2$ is selected from $C_{1-6}$alkyl; $R_3$ is selected from $C_{1-6}$alkoxy, halo-substituted-$C_{1-6}$alkyl and halo-substituted-$C_{1-6}$alkoxy; and $R_4$ is selected from $C_{1-6}$alkoxy, halo-substituted-$C_{1-6}$alkyl, halo-substituted-$C_{1-6}$alkoxy and $C_{3-8}$-heterocycloalkyl.

In a further embodiment, m, n and p are 1; $R_1$ is —OCH$_2$C(O)OH; and $R_2$ is methyl.

In another embodiment, $R_3$ is selected from methoxy, trifluoromethoxy, trifluoromethyl and morpholino.

In another embodiment, $R_4$ is selected from trifluoromethyl, methoxy, isopropyloxy and trifluoromethoxy.

Preferred compounds of the invention are selected from: {4-[2-(4-Methoxy-phenyl)-1-(4-trifluoromethyl-phenyl)-1H-imidazol-4-ylmethoxy]-2-methyl-phenoxy}-acetic acid; {4-[1-(6-Methoxy-pyridin-3-yl)-5-(4-trifluoromethoxy-phenyl)-1H-pyrazol-3-ylmethoxy]-2-methyl-phenoxy}-acetic acid; {4-[1-(4-Isopropoxy-phenyl)-5-(4-trifluoromethoxy-phenyl)-1H-[1,2,4]triazol-3-ylmethoxy]-2-methyl-phenoxy}-acetic acid; {4-[2-(4-Methoxy-phenyl)-1-(4-trifluoromethoxy-phenyl)-1H-imidazol-4-ylmethoxy]-2-methyl-phenoxy}-acetic acid; {4-[1-(4-Isopropoxy-phenyl)-2-(4-trifluoromethyl-phenyl)-1H-imidazol-4-ylmethoxy]-2-methyl-phenoxy}-acetic acid; {4-[1-(4-Methoxy-phenyl)-2-(4-trifluoromethyl-phenyl)-1H-imidazol-4-ylmethoxy]-2-methyl-phenoxy}-acetic acid; {2-Methyl-4-[1-(4-trifluoromethoxy-phenyl)-2-(4-trifluoromethyl-phenyl)-1H-imidazol-4-ylmethoxy]-phenoxy}-acetic acid; {4-[1-(6-Methoxy-pyridin-3-yl)-2-(4-trifluoromethyl-phenyl)-1H-imidazol-4-ylmethoxy]-2-methyl-phenoxy}-acetic acid; {4-[1-(4-Isopropoxy-phenyl)-2-(4-trifluoromethoxy-phenyl)-1H-imidazol-4-ylmethoxy]-2-methyl-phenoxy}-acetic acid; {4-[1-(4-Methoxy-phenyl)-2-(4-trifluoromethoxy-phenyl)-1H-imidazol-4-ylmethoxy]-2-methyl-phenoxy}-acetic acid; {4-[1,2-Bis-(4-trifluoromethoxy-phenyl)-1H-imidazol-4-ylmethoxy]-2-methyl-phenoxy}-acetic acid; {4-[1-(6-Methoxy-pyridin-3-yl)-2-(4-trifluoromethoxy-phenyl)-1H-imidazol-4-ylmethoxy]-2-methyl-phenoxy}-acetic acid; {4-[5-(4-Methoxy-phenyl)-1-(4-trifluoromethyl-phenyl)-1H-pyrazol-3-ylmethoxy]-2-methyl-phenoxy}-acetic acid; {4-[5-(4-Methoxy-phenyl)-1-(3-trifluoromethyl-phenyl)-1H-pyrazol-3-ylmethoxy]-2-methyl-phenoxy}-acetic acid; {4-[5-(4-Methoxy-phenyl)-1-(4-trifluoromethoxy-phenyl)-1H-pyrazol-3-ylmethoxy]-2-methyl-phenoxy}-acetic acid; {4-[1,5-Bis-(4-methoxy-phenyl)-1H-pyrazol-3-ylmethoxy]-2-methyl-phenoxy}-acetic acid; {2-Methyl-4-[5-(4-morpholin-4-yl-phenyl)-1-(4-trifluoromethyl-phenyl)-1H-pyrazol-3-ylmethoxy]-phenoxy}-acetic acid; {2-Methyl-4-[5-(4-morpholin-4-yl-phenyl)-1-(3-trifluoromethyl-phenyl)-1H-pyrazol-3-ylmethoxy]-phenoxy}-acetic acid; {2-Methyl-4-[5-(4-morpholin-4-yl-phenyl)-1-(4-trifluoromethoxy-phenyl)-1H-pyrazol-3-ylmethoxy]-phenoxy}-acetic acid; {4-[1-(4-Methoxy-phenyl)-5-(4-morpholin-4-yl-phenyl)-1H-pyrazol-3-ylmethoxy]-2-methyl-phenoxy}-acetic acid; {2-Methyl-4-[5-(3-trifluoromethoxy-phenyl)-1-(4-trifluoromethyl-phenyl)-1H-pyrazol-3-ylmethoxy]-phenoxy}-acetic acid; {2-Methyl-4-[5-(3-trifluoromethoxy-phenyl)-1-(3-trifluoromethyl-phenyl)-1H-pyrazol-3-ylmethoxy]-phenoxy}-acetic acid; {2-Methyl-4-[1-(4-trifluoromethoxy-phenyl)-5-(3-trifluoromethoxy-phenyl)-1H-pyrazol-3-ylmethoxy]-phenoxy}-acetic acid; {4-[1-(4-Methoxy-phenyl)-5-(3-trifluoromethoxy-phenyl)-1H-pyrazol-3-ylmethoxy]-2-methyl-phenoxy}-acetic acid; {4-[1,5-Bis-(4-trifluoromethoxy-phenyl)-1H-pyrazol-3-ylmethoxy]-2-methyl-phenoxy}-acetic acid; {4-[1-(4-Methoxy-phenyl)-5-(4-trifluoromethoxy-phenyl)-1H-pyrazol-3-ylmethoxy]-2-methyl-phenoxy}-acetic acid; {2-Methyl-4-[1-(4-trifluoromethoxy-phenyl)-5-(4-trifluoromethyl-phenyl)-1H-pyrazol-3-ylmethoxy]-phenoxy}-acetic acid; {4-[1-(4-Methoxy-phenyl)-5-(4-trifluoromethyl-phenyl)-1H-pyrazol-3-ylmethoxy]-2-methyl-phenoxy}-acetic acid; {4-[5-(4-Methoxy-phenyl)-1-(4-trifluoromethoxy-phenyl)-1H-[1,2,4]triazol-3-ylmethoxy]-2-methyl-phenoxy}-acetic acid; {4-[5-(4-Methoxy-phenyl)-1-(3-trifluoromethoxy-phenyl)-1H-[1,2,4]triazol-3-ylmethoxy]-2-methyl-phenoxy}-acetic acid; {4-[1-(4-Isopropoxy-phenyl)-5-(4-trifluoromethyl-phenyl)-1H-[1,2,4]triazol-3-ylmethoxy]-2-methyl-phenoxy}-acetic acid; {4-[1-(6-Methoxy-pyridin-3-yl)-5-(4-trifluoromethyl-phenyl)-1H-[1,2,4]triazol-3-ylmethoxy]-2-methyl-phenoxy}-acetic acid; {4-[1-(6-Methoxy-pyridin-3-yl)-5-(4-trifluoromethoxy-phenyl)-1H-[1,2,4]triazol-3-ylmethoxy]-2-methyl-phenoxy}-acetic acid; {4-[5-(5-Chloro-benzofuran-2-yl)-1-(4-isopropoxy-phenyl)-1H-[1,2,4]triazol-3-ylmethoxy]-2-methyl-phenoxy}-acetic acid; {4-[1-(4-Isopropoxy-phenyl)-5-quinolin-3-yl-1H-[1,2,4]triazol-3-ylmethoxy]-2-methyl-phenoxy}-acetic acid; {4-[1-(4-Isopropoxy-phenyl)-5-(3-trifluoromethyl-phenyl)-1H-[1,2,4]triazol-3-ylmethoxy]-2-methyl-phenoxy}-acetic acid; {4-[5-[1-(4-Fluoro-phenyl)-5-methyl-1H-pyrazol-4-yl]-1-(4-isopropoxy-phenyl)-1H-[1,2,4]triazol-3-ylmethoxy]-2-methyl-phenoxy}-acetic acid; {4-[1-(4-Isopropoxy-phenyl)-5-naphthalen-2-yl-1H-[1,2,4]triazol-3-ylmethoxy]-2-methyl-phenoxy}-acetic acid; {4-[5-(4-tert-Butyl-phenyl)-1-(4-isopropoxy-phenyl)-1H-[1,2,4]triazol-3-ylmethoxy]-2-methyl-phenoxy}-acetic acid; {4-[1-(4-Isopropoxy-phenyl)-5-(4-propyl-phenyl)-1H-[1,2,4]triazol-3-ylmethoxy]-2-methyl-phenoxy}-acetic acid; {4-[1-(4-Isopropoxy-phenyl)-5-(3-trifluoromethoxy-phenyl)-1H-[1,2,4]triazol-3-ylmethoxy]-2-methyl-phenoxy}-acetic acid; {2-Methyl-4-[1-p-tolyl-5-(4-trifluoromethoxy-phenyl)-1H-[1,2,4]triazol-3-ylmethoxy]-phenoxy}-acetic acid; {2-Methyl-4-[1-(4- methylsulfanyl-phenyl)-5-(4-trifluoromethoxy-phenyl)-1H-[1,2,4]triazol-3-ylmethoxy]-phenoxy}-acetic acid; and {2-Methyl-4-[5-(4-trifluoromethoxy-phenyl)-1-(3-trifluoromethyl-phenyl)-1H-[1,2,4]triazol-3-ylmethoxy]-phenoxy}-acetic acid.

These compounds of Formula I are detailed in the Examples and table 1, infra.

Pharmacology and Utility

Compounds of the invention modulate the activity of PPARs and, as such, are useful for treating diseases or disorders in which PPARs contributes to the pathology and/or symptomology of the disease. This invention further provides compounds of this invention for use in the preparation of medicaments for the treatment of diseases or disorders in which PPARs contributes to the pathology and/or symptomology of the disease.

Such compounds may therefore be employed for the treatment of prophylaxis, dyslipidemia, hyperlipidemia, hypercholesteremia, atherosclerosis, atherogenesis, hypertriglyceridemia, heart failure, hyper cholesteremia, myocardial infarction, vascular diseases, cardiovascular diseases, hypertension, obesity, cachexia, HIV wasting syndrome, inflammation, arthritis, cancer, Alzheimer's disease, anorexia, anorexia nervosa, bulimia, skin disorders, respiratory diseases, ophthalmic disorders, IBDs (irritable bowel disease), ulcerative colitis and Crohn's disease. Preferably for the treatment of prophylaxis, dyslipidemia, hyperlipidemia, hypercholesteremia, atherosclerosis, atherogenesis, hypertriglyceridemia, cardiovascular diseases, hypertension, obesity, inflammation, cancer, skin disorders, IBDs (irritable bowel disease), ulcerative colitis and Crohn's disease.

Compounds of the invention can also be employed to treat long term critical illness, increase muscle mass and/or muscle strength, increase lean body mass, maintain muscle strength and function in the elderly, enhance muscle endurance and muscle function, and reverse or prevent frailty in the elderly.

Further, the compounds of the present invention may be employed in mammals as hypoglycemic agents for the treatment and prevention of conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome X. Preferably type-1 and type-2 diabetes, Impaired Glucose Metabolism (IGM), Impaired Glucose Tolerance (IGT) and Impaired Fasting Glucose (IFG).

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of the invention or a pharmaceutically acceptable salt thereof. For any of the above uses, the required dosage will vary depending on the mode of administration, the particular condition to be treated and the effect desired. The present invention also concerns: i) a compound of the invention or a pharmaceutically acceptable salt thereof for use as a medicament; and ii) the use of a compound of the invention or a pharmaceutically acceptable salt thereof for the manufacture of a medicament for preventing or treating any of the diseases or disorders described above.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

This invention also concerns a pharmaceutical composition comprising a therapeutically effective amount of a compound as described herein in combination with one or more pharmaceutically acceptable carriers.

Compounds of the invention can be administered in therapeutically effective amounts in combination with one or more therapeutic agents (pharmaceutical combinations).

Thus, the present invention also relates to pharmaceutical combinations, such as a combined preparation or pharmaceutical composition (fixed combination), comprising: 1) a compound of the invention as defined above or a pharmaceutical acceptable salt thereof; and 2) at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPARγ agonist e.g. GI-262570;

b) hypolipidemic agents such as 3-hydroxy-3-methyl-glutaryl coenzyme A (HMG-CoA) reductase inhibitors, e.g., lovastatin, pravastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-HT$_3$ receptor and/or an agent interacting with 5-HT$_4$ receptor such as tegaserod described in tire U.S. Pat. No. 5,510,353 as example 13, tegaserod hydrogen maleate, cisapride, cilansetron;

or, in each case a pharmaceutically acceptable salt thereof; and optionally a pharmaceutically acceptable carrier.

Most preferred combination partners are tegaserod, imatinib, vildagliptin, metformin, a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid, a sulfonylurea receptor ligand, aliskiren, valsartan, orlistat or a statin such as pitavastatin, simvastatin, fluvastatin or pravastatin.

Preferably the pharmaceutical combinations contains a therapeutically effective amount of a compound of the invention as defined above, in a combination with a therapeutically effective amount of another therapeutic agent as described above, e.g., each at an effective therapeutic dose as reported in the art. Combination partners (1) and (2) can be administered together, one after the other or separately in one combined unit dosage form or in two separate unit dosage forms. The unit dosage form may also be a fixed combination.

The structure of the active agents identified by generic or trade names may be taken from the actual edition of the standard compendium "The Merck Index" or the Physician's Desk Reference or from databases, e.g. Patents International (e.g. IMS World Publications) or Current Drugs. The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

In another preferred aspect the invention concerns a pharmaceutical composition (fixed combination) comprising a therapeutically effective amount of a compound as described herein, in combination with a therapeutically effective amount of at least one active ingredient selected from the above described group a) to m), or, in each case a pharmaceutically acceptable salt thereof.

A pharmaceutical composition or combination as described herein for the manufacture of a medicament for the treatment of for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, IBDs (irritable bowel disease), ulcerative colitis, Crohn's disease, conditions in which impaired glucose tolerance, hyperglycemia and insulin resistance are implicated, such as type-1 and type-2 diabetes, Impaired Glucose Metabolism (IGM), Impaired Glucose Tolerance (IGT), Impaired Fasting Glucose (IFG), and Syndrome-X.

Such therapeutic agents include estrogen, testosterone, a selective estrogen receptor modulator, a selective androgen receptor modulator, insulin, insulin derivatives and mimetics; insulin secretagogues such as the sulfonylureas, e.g., Glipizide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors, GSK3 (glycogen synthase kinase-3) inhibitors or RXR ligands; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors, e.g. isoleucin-thiazolidide; DPP728 and LAF237, hypolipidemic agents, such as 3-hydroxy-3-methyl-glutaryl coenzyme A (HMG-CoA) reductase inhibitors, e.g., lovastatin, pravastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (liver X receptor) and LXR (farnesoid X receptor) ligands, cholestyramine, fibrates, nicotinic acid and aspirin. A compound of the present invention may be administered either simultaneously, before or after the other active ingredient, either separately by the same or different route of administration or together in the same pharmaceutical formulation.

The invention also provides for pharmaceutical combinations, e.g. a kit, comprising: a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

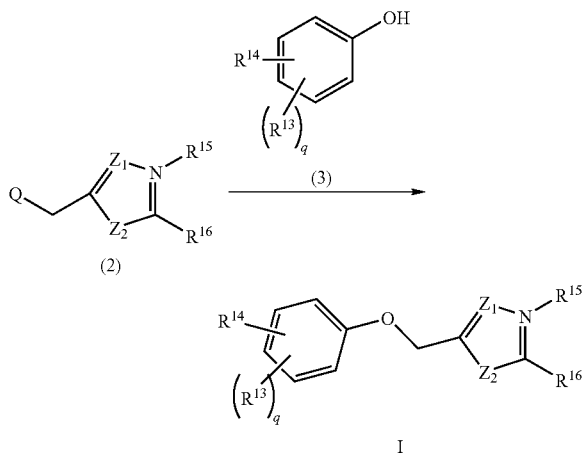

in which q, $Z_1$, $Z_2$, $R^{13}$, $R^{14}$, $R^{15}$ and $R^{16}$ are as defined in the Summary of the Invention and Q is a leaving group such as halogen, $-OS(O)_2R_{30}$ or the like (wherein $R_{30}$ is, for example, methyl). Compounds of Formula I are prepared by reacting a compound of formula 2 with a compound of formula 3 in the presence of a suitable base (for example, Cesium carbonate, and the like) and a suitable solvent (e.g., cyanomethyl, DMF, DMSO, THF, dioxane or the like). If required, the reaction can be followed by a saponification of any $R^{14}$ carboxylate ester to the corresponding acid. The reaction is carried out in the temperature range of about 0° C. to about 60° C. and takes up to about 10 hours to complete.

Detailed descriptions of the synthesis of compounds of Formula Ia, Ib, Ic and Id are detailed in the example, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamoylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates and examples that illustrate the preparation of compounds of Formula I according to the invention.

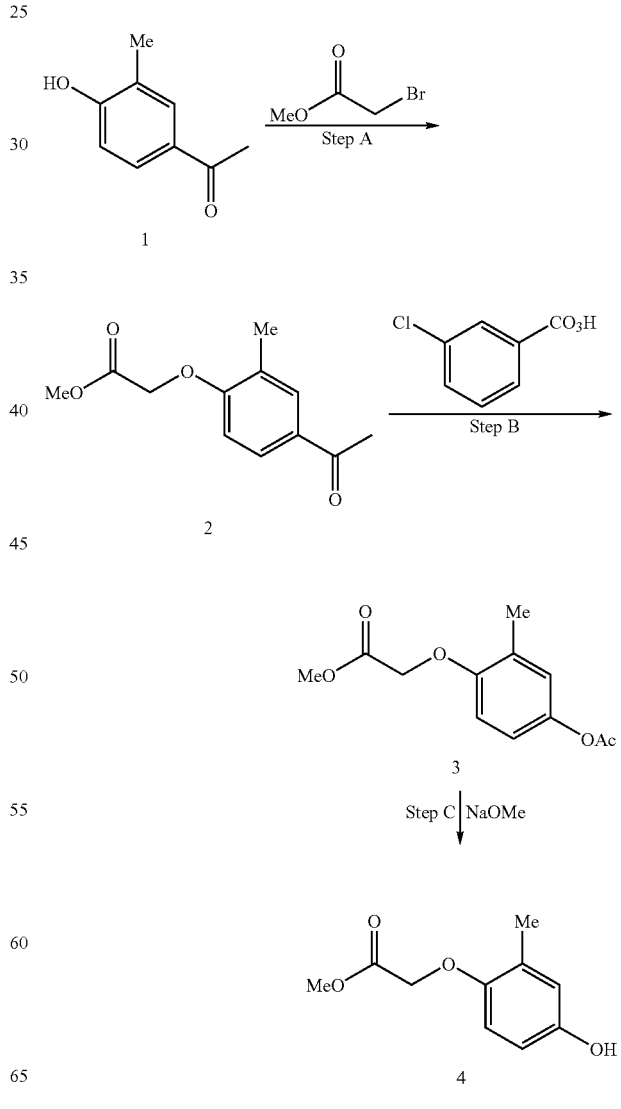

Intermediate 4

4-Hydroxy-(2-methyl-phenoxy)-acetic Acid Methyl Ester

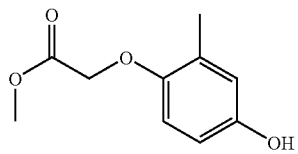

Step A: 4'-Hydroxy-3'-methylacetophenone 1 (25 g, 166.4 mmol) and methyl-bromoacetate (25.5 g, 166.4 mmol) are dissolved in MeCN (600 mL). $Cs_2CO_3$ (117.8 g, 332.9 mmol) is added and the mixture is stirred overnight at room temperature. After insoluble salts are filtered and washed with MeCN, the solvent is removed and the remainder is taken up in EtOAc and washed subsequently with 1 M HCl (3×500 mL) and $H_2O$ (2×500 mL). The organic layer is dried ($MgSO_4$), filtered and concentrated to afford 2 (35.9 g, 161.4 mmol) as a white solid.

Step B: (4-Acetyl-2-methyl-phenoxy)-acetic acid methyl ester 2 (33 g, 151.3 mmol), 77% mCPBA (54.9 g, 264.8 mmol) and p-TsOH (2.9 g, 15.1 mmol) in DCM (650 mL) are heated under reflux for 48 hours. The reaction mixture is then washed with 1 M KI (2×500 mL) and $NaHSO_3$ (2×500 mL). The organic layer is dried ($MgSO_4$), filtered and concentrated to afford 3 (28.8 g, 121.0 mmol) as a brown syrup.

Step C: A solution of (4-acetoxy-2-methyl-phenoxy)-acetic acid methyl ester 3 (25 g, 105.0 mmol) in dry MeOH (400 mL) is combined with a 0.5 M solution of NaOMe in MeOH (210 mL, 105.0 mmol) and stirred for 1 hour at room temperature. The solution is neutralized with 1 M HCl and washed with $H_2O$ (2×500 mL). The organic layer is dried ($MgSO_4$), filtered and concentrated to afford 4 (17.5 g, 89.3 mmol) as a brown solid: $^1$H-NMR (400 MHz, $CD_3OD$) δ=6.65-6.51 (m, 3H), 4.60 (s, 2H), 3.75 (s, 3H), 2.19 (s, 3H); MS calculated for $C_{10}H_{13}O_4$ (M+H$^+$) 197.1, found 197.2.

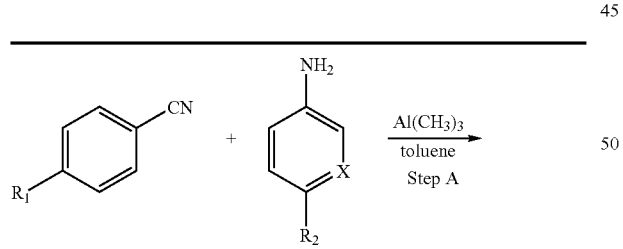

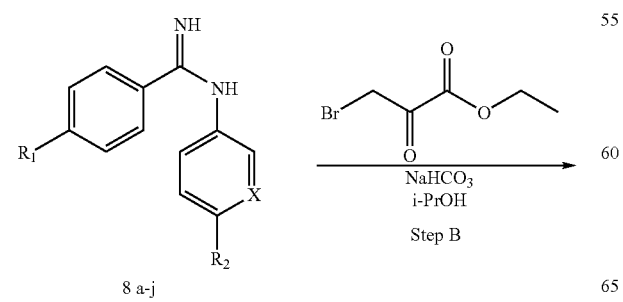

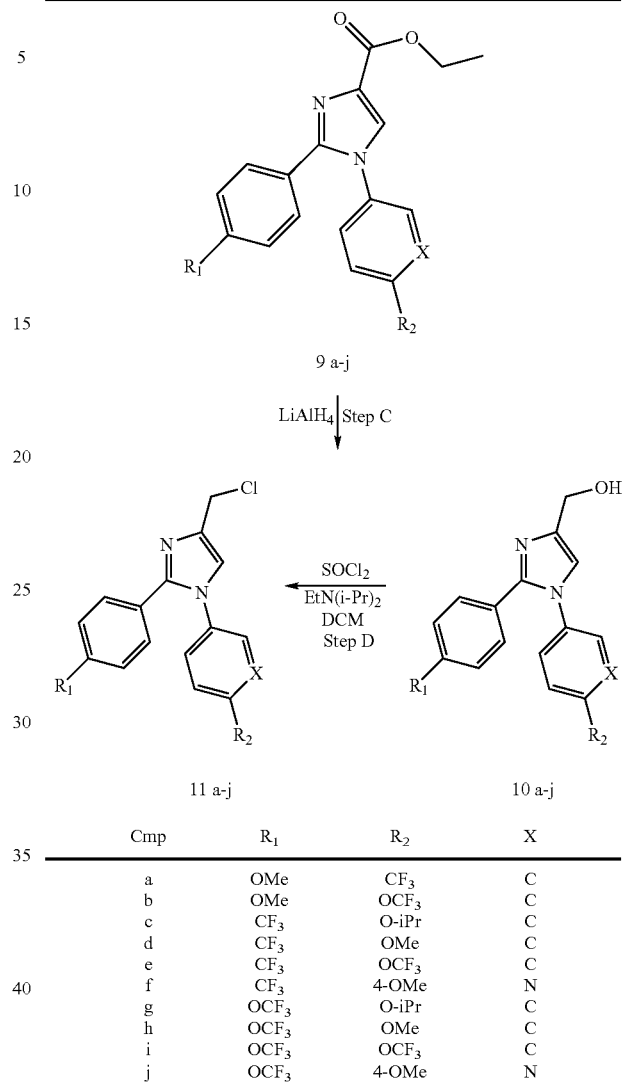

| Cmp | $R_1$ | $R_2$ | X |
|---|---|---|---|
| a | OMe | $CF_3$ | C |
| b | OMe | $OCF_3$ | C |
| c | $CF_3$ | O-iPr | C |
| d | $CF_3$ | OMe | C |
| e | $CF_3$ | $OCF_3$ | C |
| f | $CF_3$ | 4-OMe | N |
| g | $OCF_3$ | O-iPr | C |
| h | $OCF_3$ | OMe | C |
| i | $OCF_3$ | $OCF_3$ | C |
| j | $OCF_3$ | 4-OMe | N |

Intermediate 11a

4-Chloromethyl-2-(4-methoxy-phenyl)-1-(4-trifluoromethyl-phenyl)-1H-imidazole

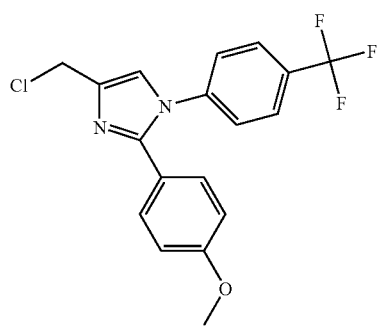

Step A: 4-Trifluoroaniline (1.0 g, 6.2 mmol) is dissolved in anhydrous toluene (50 mL) and cooled to 0° C. Trimethylaluminum (4.3 mL of 2.0 N in toluene, 8.7 mmol) is added slowly and the mixture is stirred at 0° C. for 3 hours. A solution of 4-methoxybenzonitrile (1.0 g, 7.8 mmol) in anhydrous toluene (20 mL) is added and the mixture is heated at 70° C. for 16 hours. The solution is cooled, filtered through a plug of silica gel, washed with ethyl acetate (200 mL), and concentrated to give crude 8a, which is used without further purification in step B: MS calculated for $C_{15}H_{14}F_3N_2O$ (M+H$^+$) 294.1, found 294.1.

Step B: 4-Methoxy-N-(4-trifluoromethyl-phenyl)-benzamidine 8a and sodium bicarbonate (1.0 g, 12.4 mmol) are mixed (slurry) in isopropanol (40 mL) and heated to 40° C. Ethyl bromo pyruvate (1.1 mL, 8.7 mmol) is added dropwise and the mixture is heated at 70° C. for 48 hours, then cooled and acidified with 1 N HCl (30 mL). The reaction mixture is extracted with EtOAc (2×40 mL), the organic layer is separated, dried (MgSO$_4$) and concentrated. Silica gel chromatography (0% to 40% ethyl acetate in hexanes) yielded 9a (0.80 g, 2.03 mmol) as a white powder: MS calculated for $C_{20}H_{18}F_3N_2O_3$ (M+H$^+$) 391.1, found 391.1.

Step C: 2-(4-Methoxy-phenyl)-1-(4-trifluoromethyl-phenyl)-1H-imidazole-4-carboxylic acid ethyl ester 9a (0.80 g, 2.03 mmol) is dissolved in anhydrous THF (10 mL), then LiAlH$_4$ (3.1 mL of 1.0 N in THF, 3.1 mmol) is added and the mixture is stirred at room temperature for 1 hour. The mixture is acidified by slow addition of 1 N HCl (5 mL), extracted into ethyl acetate (2×10 mL), dried (MgSO$_4$), filtered through a plug of silica gel, and washed with EtOAc (40 mL). Concentration in vacuo affords crude 10a (0.21 g, 0.59 mmol), which is used in the next step without further purification: MS calculated for $C_{18}H_{16}F_3N_2O_2$ (M+H$^+$) 348.1, found 348.1.

Step D: [2-Methoxy-phenyl-1-(4-trifluoromethyl-phenyl)-1H-imidazol-4-yl]-methanol 10a (0.1 g, 0.28 mmol) is dissolved in dichloromethane (5 mL). Diisopropyl-ethylamine (0.072 mL, 0.44 mmol) is added, followed by thionyl chloride (0.030 mL, 0.40 mmol), and the mixture is stirred for 30 minutes at room temperature. The mixture is diluted with 1 N HCl (5 mL) and extracted into dichloromethane (2×5 mL), dried (MgSO$_4$), filtered and concentrated to give 11a, which is used directly in the next step: MS calculated for $C_{18}H_{15}ClF_3N_2O$ (M+H$^+$) 367.1, found 367.1.

| Compound | Structure | Physical Data |
|---|---|---|
| 11b | 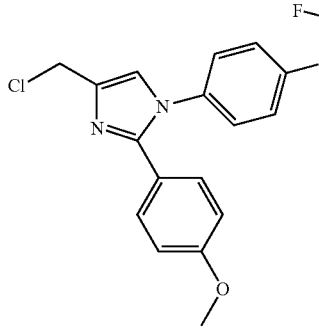 | MS calculated for $C_{18}H_{15}ClF_3N_2O_2$ (M + H$^+$) 383.1, found 383.1 |
| 11c | 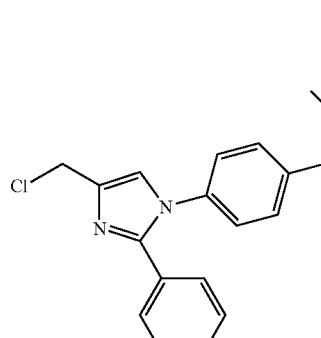 | MS calculated for $C_{20}H_{19}ClF_3N_2O$ (M + H$^+$) 395.1, found 395.1 |

-continued

| Compound | Structure | Physical Data |
|---|---|---|
| 11d | 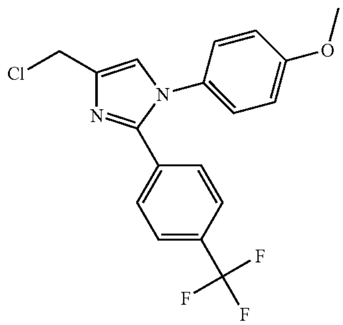 | $^1$H nmr (400 MHz, CDCl$_3$) δ = 7.59(d, J = 8.4 Hz, 2 H), 7.53(d, J = 8.4 Hz, 2 H), 7.16(s, 1 H), 7.12(d, J = 8.4 Hz, 2 H), 6.93(d, J = 8.4 Hz, 2 H), 4.73 (s, 2 H), 3.80(s, 3 H). MS calculated for C$_{18}$H$_{15}$ClF$_3$N$_2$O (M + H$^+$) 367.1, found 367.1 |
| 11e | 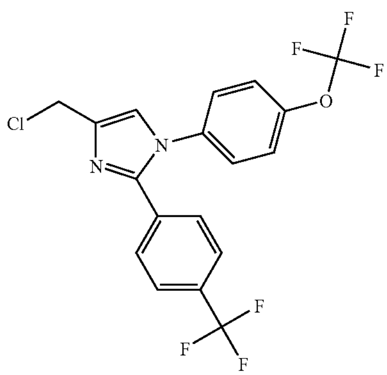 | MS calculated for C$_{18}$H$_{12}$ClF$_6$N$_2$O (M + H$^+$) 421.1, found 421.1 |
| 11f | 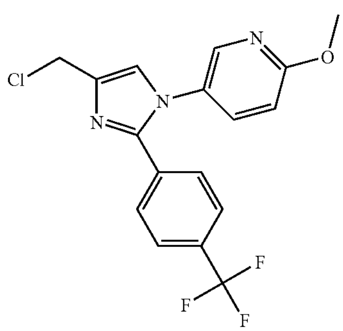 | $^1$H nmr (400 MHz, CDCl$_3$) δ = 8.16(s, 1 H), 7.69(d, J = 7.6 Hz, 2 H), 7.57 (d, J = 8.8 Hz, 2 H), 7.54(m, 1 H), 7.31(s, 1 H), 6.87(d, J = 6.4 Hz, 1 H), 4.80(s, 2 H), 3.99(s, 3 H). MS calculated for C$_{17}$H$_{14}$ClF$_3$N$_3$O (M + H$^+$) 368.1, found 368.1 |
| 11g | 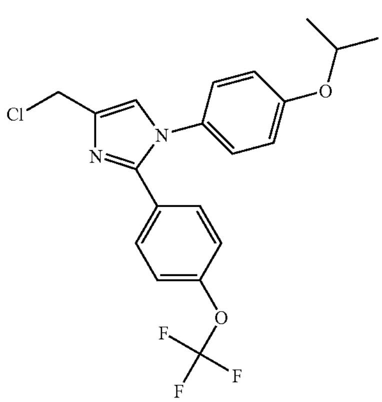 | $^1$H nmr (400 MHz, CDCl$_3$) δ = 7.53(d, J = 8.8 Hz, 2 H), 7.27(d, J = 8.8 Hz, 2 H), 7.22(s, 1 H), 7.18(d, J = 8.8 Hz, 2 H), 6.98(d, J = 8.8 Hz, 2 H), 4.79 (s, 2 H), 4.62(m, 1 H), 1.39(s, 3 H), 1.38(s, 3 H). MS calculated for C$_{20}$H$_{19}$ClF$_3$N$_2$O$_2$ (M + H$^+$) 411.1, found 411.1 |

| Compound | Structure | Physical Data |
|---|---|---|
| 11h | 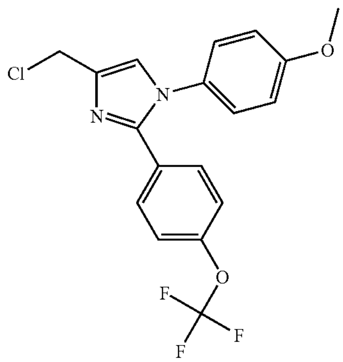 | $^1$H nmr (400 MHz, CDCl$_3$) δ = 7.54(d, J = 8.8 Hz, 2 H), 7.22(d, J = 8.4 Hz, 2 H), 7.17(m, 3 H), 7.01(d, J = 8.4 Hz, 2 H), 4.80(s, 2 H), 3.88(s, 3 H). MS calculated for C$_{18}$H$_{15}$ClF$_3$N$_2$O$_2$ (M + H$^+$) 383.1, found 383.1 |
| 11i | 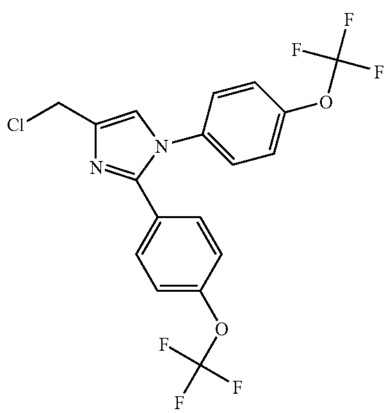 | MS calculated for C$_{18}$H$_{12}$ClF$_6$N$_2$O$_2$ (M + H$^+$) 437.0, found 437.1 |
| 11j | 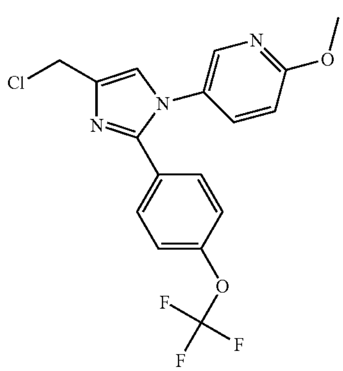 | MS calculated for C$_{17}$H$_{14}$ClF$_3$N$_3$O$_2$ (M + H$^+$) 384.1, found 384.1 |

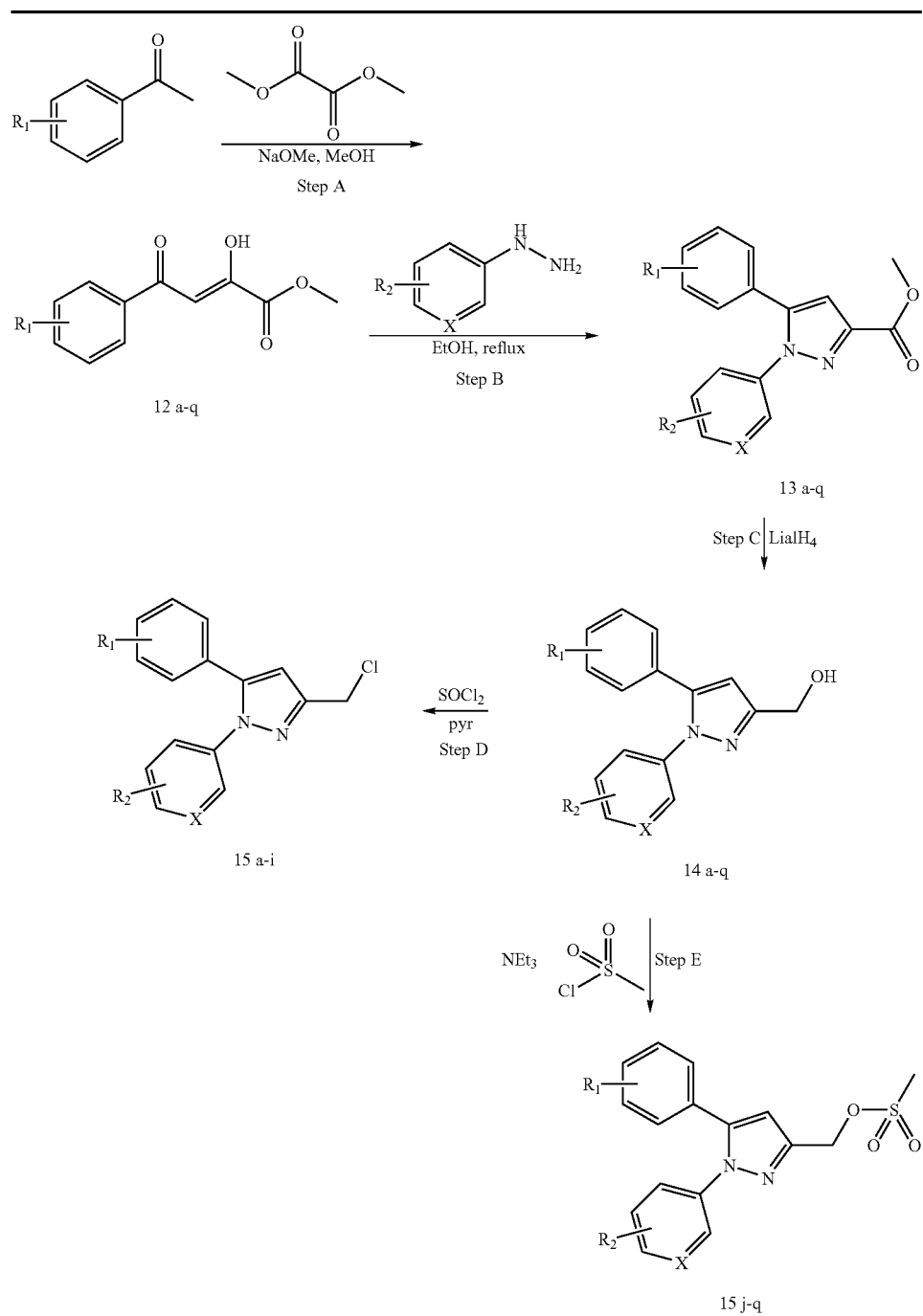
| Cmp | R₁ | R₂ | X |
|---|---|---|---|
| a | 4-OCF$_3$ | 4-OMe | N |
| b | 4-OMe | 3-CF$_3$ | C |
| c | 4-OMe | 4-OCF$_3$ | C |
| d | 4-OMe | 4-OMe | C |
| e | 4-OCF$_3$ | 4-OCF$_3$ | C |
| f | 4-OCF$_3$ | 4-OMe | C |
| g | 4-OMe | 4-CF$_3$ | C |
| h | 4-CF$_3$ | 4-OCF$_3$ | C |
| i | 4-CF$_3$ | 4-OMe | C |
| j | 4-morph | 4-CF$_3$ | C |
| k | 4-morph | 3-CF$_3$ | C |
| l | 4-morph | 4-OCF$_3$ | C |

| | | | |
|---|---|---|---|
| m | 4-morph | 4-OMe | C |
| n | 3-OCF$_3$ | 4-CF$_3$ | C |
| o | 3-OCF$_3$ | 3-CF$_3$ | C |
| p | 3-OCF$_3$ | 4-OCF$_3$ | C |
| q | 3-OCF$_3$ | 4-OMe | C |

Intermediate 15a

5-[3-Chloromethyl-5-(4-trifluoromethoxy-phenyl)-pyrazol-1-yl]-2-methoxy-pyridine

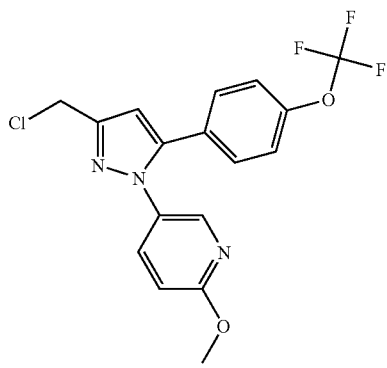

Step A: 4'-Trifluoromethoxyacetophenone (9.3 g, 45.4 mmol) is dissolved in anhydrous THF (200 mL). Sodium hydride (3.0 g of 60% dispersion in oil, 75 mmol) is added and the mixture is heated at 40° C. for 3 hours. Dimethyl oxalate (10.75 g, 91 mmol) is dissolved in anhydrous THF (100 mL), added to the mixture and stirred at 40° C. for 1 hour. The mixture is cooled, acidified with 1 N HCl (100 mL), and extracted into ethyl acetate (2×300 mL). The organic layers are combined and washed with 1 N HCl (100 mL) and brine (50 mL), dried (MgSO$_4$), filtered and concentrated. The residue is triturated with hexanes and filtered to give 12a as pale yellow crystals: $^1$H-NMR (400 MHz, CDCl$_3$) δ=7.96 (d, J=8.8 Hz, 2H), 7.26 (d, J=8.8 Hz, 2H) 6.97 (s, 1H), 3.87 (s, 3H); MS calculated for C$_{12}$H$_{10}$F$_3$O$_5$ (M+H$^+$) 291.0, found 291.0.

Step B: 2-Hydroxy-4-oxo-4-(4-trifluoromethoxy-phenyl)-but-2-enoic acid methyl ester 12a (7.5 g, 25.8 mmol) and (6-Methoxy-pyridin-3-yl)-hydrazine hydrochloride (5.43 g, 31.0 mmol) are dissolved in methanol (100 mL), and heated at reflux for 3 hours. The mixture is evaporated and purified by silica gel chromatography (0% to 40% ethyl acetate in hexanes) to give 13a (4.70 g, 11.9 mmol) as a white powder: $^1$H-NMR (400 MHz, CDCl$_3$) δ=8.09 (d, J=2.8 Hz, 1H), 7.57 (dd, J=2.8, 8.8 Hz, 1H), 7.27 (d, J=8.8 Hz, 2H), 7.19 (d, J=8.4 Hz, 2H), 7.06 (s, 1H), 6.76 (d, J=8.8 Hz, 1H), 3.98 (s, 3H), 3.95 (s, 3H); MS calculated for C$_{18}$H$_{15}$F$_3$N$_3$O$_4$ (M+H$^+$) 394.1, found 394.1.

Step C: 1-(6-Methoxy-pyridin-3-yl)-5-(4-trifluoromethoxy-phenyl)-1H-pyrazole-3-carboxylic acid methyl ester 13a (4.7 g, 11.95 mmol) is dissolved in anhydrous THF (10 mL) and cooled to 0° C., then LiAlH$_4$ (17.9 mL of 1.0 N in THF, 17.9 mmol) is added and the mixture is stirred at room temperature for 1 hour. The mixture is acidified through slow addition of 1 N HCl (150 mL), extracted into EtOAc (2×200 mL), dried (MgSO$_4$), filtered and concentrated to give 14a, which is used in the next step without further purification: $^1$H-NMR (400 MHz, CDCl$_3$) δ=8.04 (d, J=2.8 Hz, 1H), 7.52 (dd, J=2.8, 8.8 Hz, 1H), 7.24 (d, J=8.8 Hz, 2H), 7.17 (d, J=8.4 Hz, 2H), 6.73 (dd, J=4.0, 8.4 Hz, 1H), 6.52 (d, J=3.6 Hz, 1H), 4.77 (s, 2H), 3.93 (s, 3H); MS calculated for C$_{17}$H$_{15}$F$_3$N$_3$O$_3$ (M+H$^+$) 366.1, found 366.1.

Step D: [1-(6-Methoxy-pyridin-3-yl)-5-(4-trifluoromethoxy-phenyl)-1H-pyrazol-3-yl]-methanol 14a (3.68 g, 10.1 mmol) is dissolved in dichloromethane (100 mL) and cooled to 0° C. Diisopropylethylamine (2.63 mL, 15.1 mmol) is added, followed by thionyl chloride (1.1 mL, 15.1 mmol), and the mixture is stirred at 0° C. for 2 hours. The mixture is poured into saturated NaHCO$_3$ solution (100 mL), extracted into dichloromethane (2×100 mL), dried (MgSO$_4$), filtered and concentrated. Silica gel chromatography (0% to 40% ethyl acetate in hexanes) yielded 15a: $^1$H-NMR (400 MHz, CDCl$_3$) δ=7.93 (d, J=2.4 Hz, 1H), 7.41 (dd, J=2.4, 8.8 Hz, 1H), 7.14 (d, J=8.4 Hz, 2H), 7.05 (d, J=8.8 Hz, 2H), 6.63 (d, J=8.8 Hz, 1H), 6.48 (s, 1H), 4.56 (s, 2H), 3.82 (s, 3H); MS calculated for C$_{17}$H$_{14}$ClF$_3$N$_3$O$_2$ (M+H$^+$) 384.1, found 384.1.

| Compound | Structure | Physical Data |
|---|---|---|
| 15b | 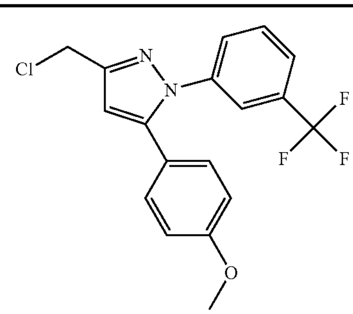 | MS calculated for C$_{18}$H$_{15}$ClF$_3$N$_2$O (M + H$^+$) 367.1, found 367.1 |

-continued

| Compound | Structure | Physical Data |
|---|---|---|
| 15c | 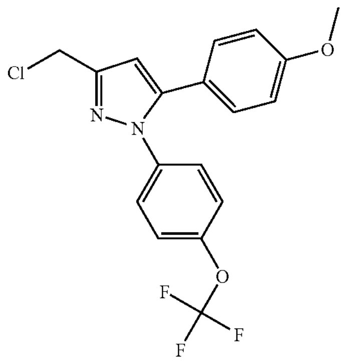 | MS calculated for $C_{18}H_{14}ClF_3N_2O_2$ (M + H$^+$) 383.1, found 383.1 |
| 15d | 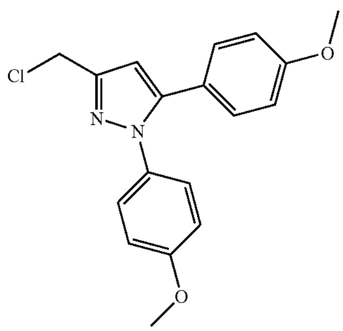 | MS calculated for $C_{18}H_{18}ClN_2O_2$ (M + H$^+$) 329.1, found 329.1 |
| 15e | 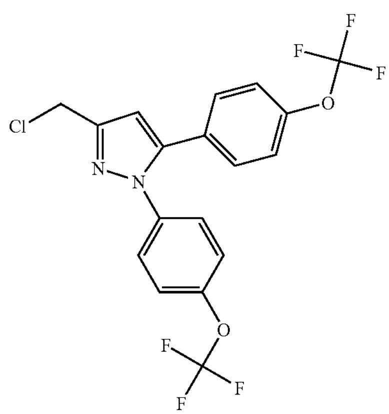 | MS calculated for $C_{18}H_{12}ClF_6N_2O_2$ (M + H$^+$) 437.0, found 437.1 |
| 15f | 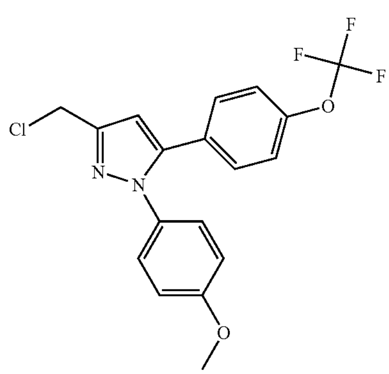 | MS calculated for $C_{18}H_{15}ClF_3N_2O_2$ (M + H$^+$) 383.0, found 383.1 |

-continued
| Compound | Structure | Physical Data |
|---|---|---|
| 15g | 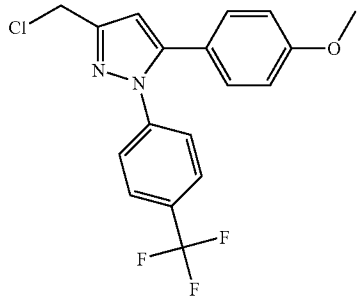 | MS calculated for $C_{18}H_{15}ClF_3N_2O$ (M + H$^+$) 367.1, found 367.1 |
| 15h | 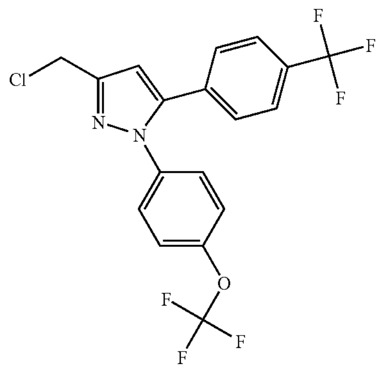 | MS calculated for $C_{18}H_{12}ClF_6N_2O$ (M + H$^+$) 421.1, found 421.1 |
| 15i | 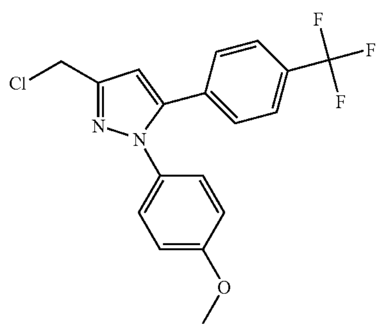 | MS calculated for $C_{18}H_{15}ClF_3N_2O$ (M + H$^+$) 367.1, found 367.1 |
Intermediate 15j
Methanesulfonic Acid 5-(4-morpholin-4-yl-phenyl)-1-(4-trifluoromethyl-phenyl)-1H-pyrazol-3-ylmethyl Ester
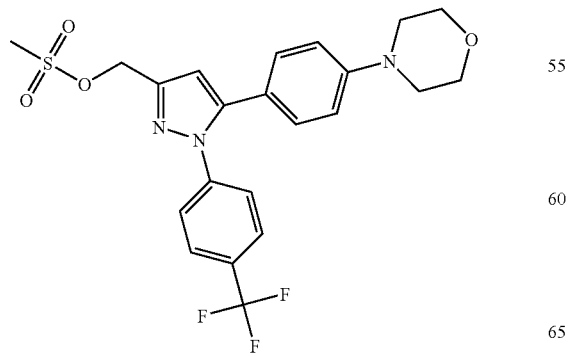

Following the procedure of Intermediate 15a, except substituting 4'-morpholino-acetophenone for 4-methoxyacetophenone in Step A, and formation of the mesylate instead of the chloride via Step E:

Step E: Alcohol 14e (0.47 mmol) is dissolved in a mixture of dichloromethane (5 mL) and triethylamine (232 μL, 1.65 mmol), then methanesulfonyl chloride (47 μL, 0.6 mmol) is added and the mixture is stirred at room temperature for 2 hours. The mixture is poured into 1 N HCl (10 mL), extracted with dichloromethane (2×10 mL), dried (MgSO$_4$), filtered and concentrated to give 15e, which is used without purification in the next step: MS calculated for $C_{22}H_{23}F_3N_3O_4S$ (M+H$^+$) 482.1, found 482.1.

| Compound | Structure | Physical Data |
|---|---|---|
| 15k | 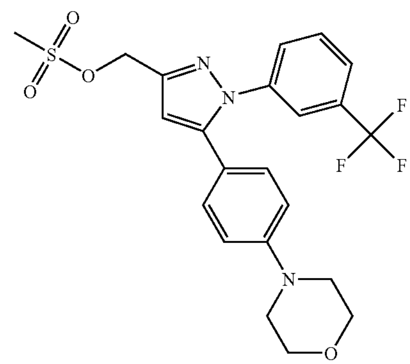 | MS calculated for $C_{22}H_{23}F_3N_3O_4S$ (M + H$^+$) 482.1, found 482.1 |
| 15l | 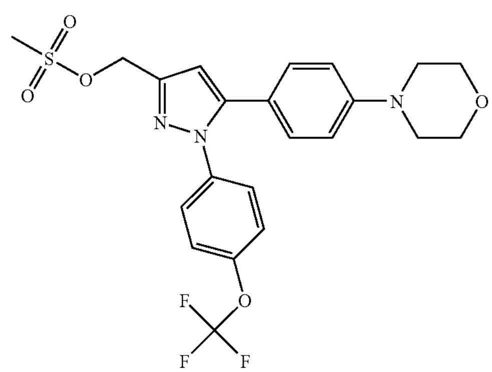 | MS calculated for $C_{22}H_{22}F_3N_3O_5S$ (M + H$^+$) 498.1, found 498.1 |
| 15m | 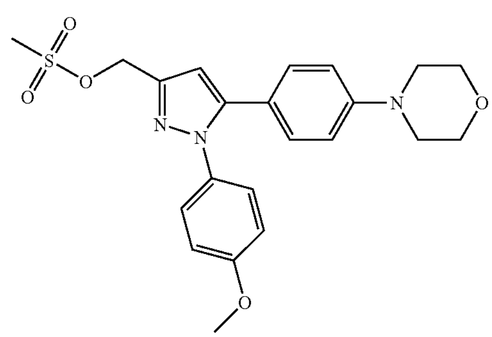 | MS calculated for $C_{22}H_{26}N_3O_5S$ (M + H$^+$) 444.2, found 444.1 |

-continued

| Compound | Structure | Physical Data |
|---|---|---|
| 15n | 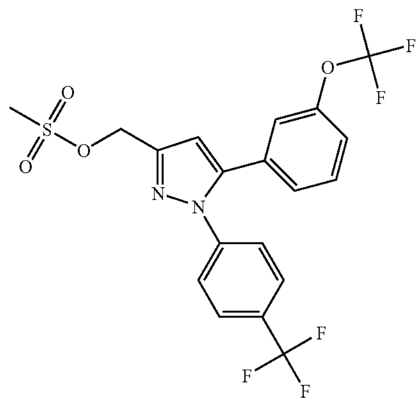 | MS calculated for $C_{19}H_{15}F_6N_2O_4S$ (M + H$^+$) 481.1, found 481.1 |
| 15o | 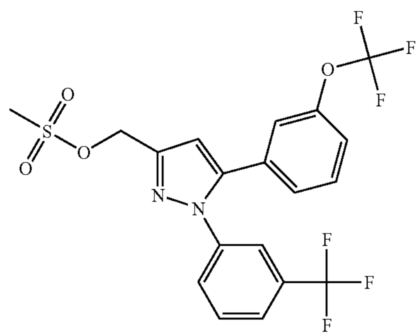 | MS calculated for $C_{19}H_{15}F_6N_2O_4S$ (M + H$^+$) 481.1, found 481.1 |
| 15p | 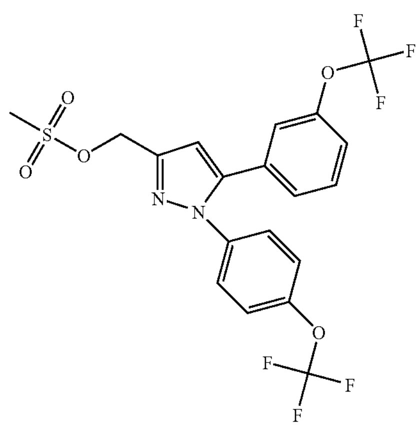 | MS calculated for $C_{19}H_{15}F_6N_2O_5S$ (M + H$^+$) 497.0, found 497.1 |
| 15q | 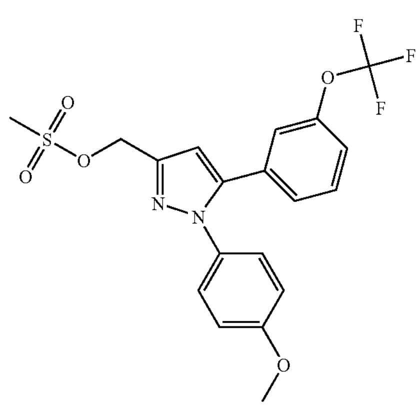 | MS calculated for $C_{19}H_{18}F_3N_2O_5S$ (M + H$^+$) 443.1, found 443.1 |

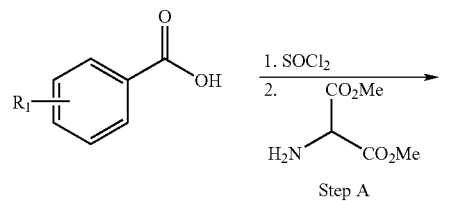
Step A
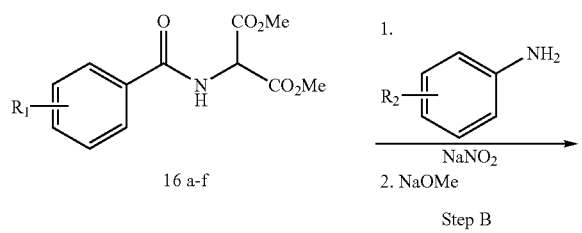
16 a-f
Step B
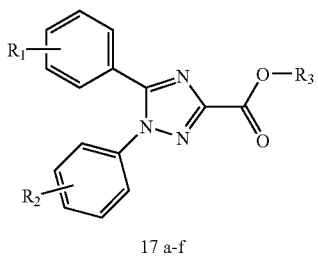
17 a-f
Step C | $R_3$ = H or Me
LiAlH$_4$
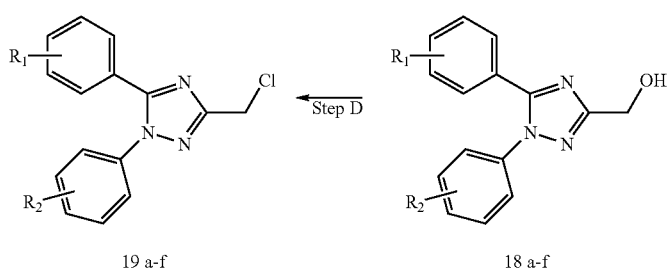
19 a-f     18 a-f
| Cmp | $R_1$ | $R_2$ | X |
|---|---|---|---|
| a | 4-OCF$_3$ | 4-OiPr | C |
| b | 4-OMe | 3-OCF$_3$ | C |
| c | 4-CF$_3$ | 4-OiPr | C |
| d | 4-CF$_3$ | 4-OMe | N |
| e | 4-OMe | 4-OCF$_3$ | C |
| f | 4-OCF$_3$ | 4-OMe | N |

Intermediate 19a

3-Chloromethyl-1-(4-isopropoxy-phenyl)-5-(4-trifluoromethoxy-phenyl)-1H-[1,2,4]triazole

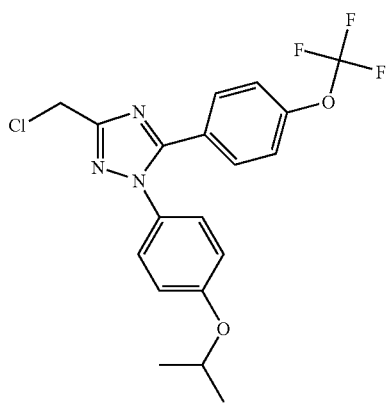

Step A: 4-(Trifluoromethoxy)benzoic acid (8 g, 38.8 mmol) is heated at reflux in thionyl chloride (50 mL) for 1 hour. The residue is concentrated in vacuo, and washed with dichloromethane (2×50 mL) and evaporated. The residue is redissolved in dichloromethane (100 mL), dimethyl aminomalonate (8.55 g, 46.6 mmol) is added and the mixture is heated at 40° C. for 24 hours. The mixture is poured into saturated NaHCO$_3$ solution (20 mL), extracted with dichloromethane (2×10 mL), washed with water (10 mL) and brine (10 mL), dried (MgSO$_4$), filtered and evaporated to give 16a as a crystalline material which is used in the next step without further purification: $^1$H-NMR (400 MHz, CDCl$_3$) δ=7.89 (d, J=8.4 Hz, 2H), 7.28 (d, J=8.0 Hz, 2H), 7.16 (d, J=5.4 Hz, 1H), 5.37 (d, J=6.0 Hz, 1H), 3.85 (s, 6H); MS calculated for C$_{13}$H$_{13}$F$_3$NO$_6$ (M+H$^+$) 336.1, found 336.0.

Step B: 4-Isopropoxyaniline (7.04 g, 46.6 mmol) is dissolved in a mixture of acetic acid (50 mL) and concentrated HCl (10 mL), then a solution of sodium nitrite (3.35 g, 48.5 mmol) in water (20 mL) is added dropwise at 0° C. and stirred for 15 minutes. The mixture is cooled to −10° C. then a solution of 2-(4-trifluoromethoxy-benzoylamino)-malonic acid dimethyl ester 16a (13 g, 38.8 mmol) in acetone (100 mL) is added dropwise, followed by a solution of potassium carbonate (52 g, 380 mmol) in water (150 mL). The resulting solution is stirred at 0° C. for 1 hour, then extracted with EtOAc (2×300 mL), dried (MgSO$_4$), filtered and concentrated in vacuo. The residue is dissolved in anhydrous MeOH (100 mL), then sodium methoxide (155 mL of 0.5 N in MeOH, 77.6 mmol) is added and the mixture is stirred at room temperature for 18 hours. The reaction is poured into 1 N HCl (200 mL), extracted into EtOAc (2×300 mL), dried (MgSO$_4$), filtered and evaporated to give a mixture of acid and ester 17a, the bulk of which is used without further purification in Step C. A small sample is purified on reverse phase HPLC (H$_2$O/MeCN gradient) to afford the acid as a yellow oil: $^1$H-NMR (400 MHz, CDCl$_3$) δ=7.63 (d, J=8.8 Hz, 2H), 7.29 (d, J=8.8 Hz, 2H), 7.18 (d, J=8.0 Hz, 2H), 6.92 (d, J=8.4 Hz, 2H), 4.58 (m, 1H), 1.36 (s, 3H), 1.35 (s, 3H); MS calculated for C$_{19}$H$_{17}$F$_3$N$_3$O$_4$ (M+H$^+$) 408.1, found 408.0.

Step C: Crude 1-(4-isopropoxy-phenyl)-5-(4-trifluoromethoxy-phenyl)-1H-[1,2,4]triazole-3-carboxylic acid 17a (38.8 mmol) is dissolved in anhydrous THF (100 mL), then LiAlH$_4$ (58.2 mL of 1.0 N in THF, 58.2 mmol) is added and the mixture is stirred at room temperature for 1 hour. The mixture is acidified by slow addition of 1 N HCl (50 mL), extracted into ethyl acetate (3×100 mL), dried (MgSO$_4$), filtered through a plug of silica gel, and washed with EtOAc (100 mL). Concentration in vacuo afforded 18a, the bulk of which is used directly in the next step without further purification. A small sample is purified on reverse phase HPLC (H$_2$O/MeCN gradient) to afford the acid as a yellow oil: $^1$H-NMR (400 MHz, CDCl$_3$) δ=7.53 (d, J=8.8 Hz, 2H), 7.21 (d, J=8.8 Hz, 2H), 7.16 (d, J=8.0 Hz, 2H), 6.90 (d, J=8.8 Hz, 2H), 4.82 (s, 2H), 4.57 (m, 1H), 1.36 (s, 3H), 1.34 (s, 3H); MS calculated for C$_{19}$H$_{19}$F$_3$N$_3$O$_3$ (M+H$^+$) 394.1, found 394.1.

Step D: [1-(4-Isopropoxy-phenyl)-5-(4-trifluoromethoxyphenyl)-1H-[1,2,4]triazol-3-yl]-methanol 18a (38 mmol) is dissolved in dichloromethane (150 mL) and cooled to 0° C. Diisopropylethylamine (10 mL, 57 mmol) is added, followed by thionyl chloride (4.2 mL, 57 mmol), and the mixture is stirred for 2 hours at room temperature. The mixture is diluted with 1 N HCl (50 mL) and extracted into dichloromethane (2×100 mL), dried (MgSO$_4$), and filtered. Silica gel chromatography (0% to 40% ethyl acetate in hexanes) yields 19a as a yellow oil: $^1$H-NMR (400 MHz, CDCl$_3$) δ=7.57 (d, J=8.8 Hz, 2H), 7.24 (d, J=8.8 Hz, 2H), 7.17 (d, J=8.4 Hz, 2H), 6.92 (d, J=8.8 Hz, 2H), 4.71 (s, 2H), 4.58 (m, 1H), 1.37 (s, 3H), 1.35 (s, 3H); MS calculated for C$_{19}$H$_{18}$ClF$_3$N$_3$O$_2$ (M+H$^+$) 412.1, found 412.1.

| Compound | Structure | Physical Data |
|---|---|---|
| 19b | 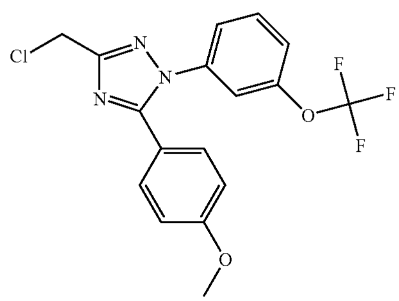 | MS calculated for C$_{17}$H$_{14}$ClF$_3$N$_3$O$_2$ (M + H$^+$) 384.1, found 384.1 |

-continued

| Compound | Structure | Physical Data |
|---|---|---|
| 19c | 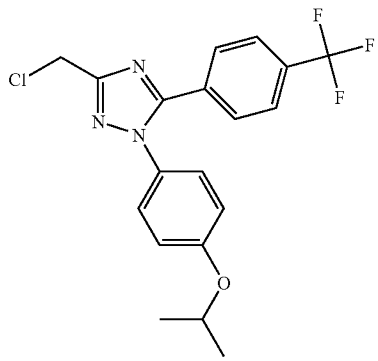 | MS calculated for C₁₇H₁₄ClF₃N₃O₂ (M + H⁺) 384.1, found 384.1 |
| 19d | 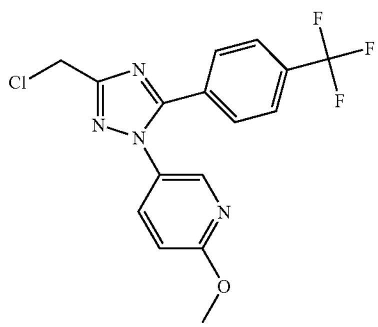 | MS calculated for C₁₆H₁₃ClF₃N₄O (M + H⁺) 369.1, found 369.1 |
| 19e | 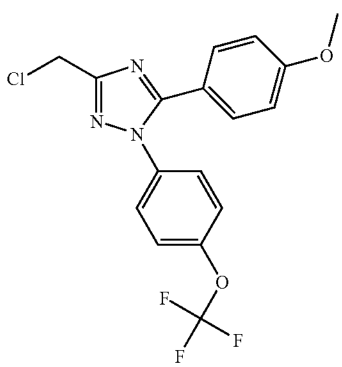 | MS calculated for C₁₇H₁₄ClF₃N₃O₂ (M + H⁺) 384.1, found 384.0 |
| 19f | 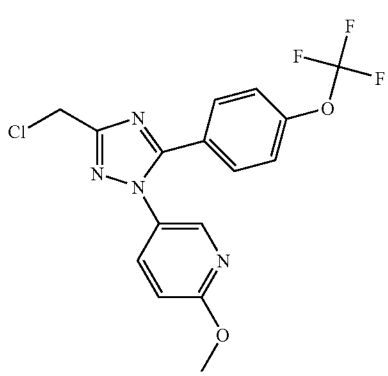 | MS calculated for C₁₆H₁₃ClF₃N₄O₂ (M + H⁺) 385.1, found 385.1 |

-continued

| Compound | Structure | Physical Data |
|---|---|---|
| 19g | 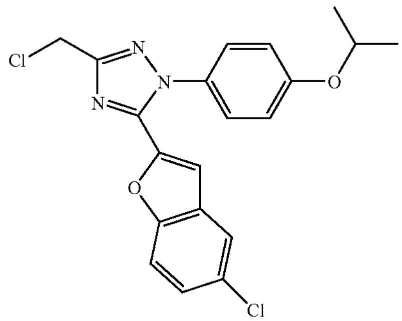 | MS calculated for $C_{20}H_{18}Cl_2N_3O_2$ (M + H$^+$) 402.0, found 402.1 |
| 19h | 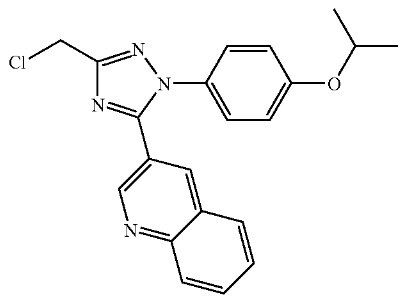 | MS calculated for $C_{21}H_{20}ClN_4O$ (M + H$^+$) 379.1, found 379.2 |
| 19i | 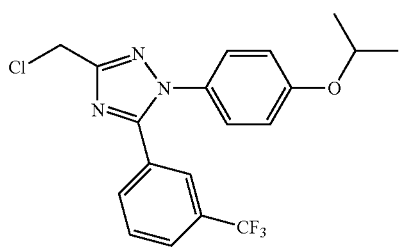 | MS calculated for $C_{19}H_{18}ClF_3N_3O$ (M + H$^+$) 396.1, found 396.1 |
| 19j | 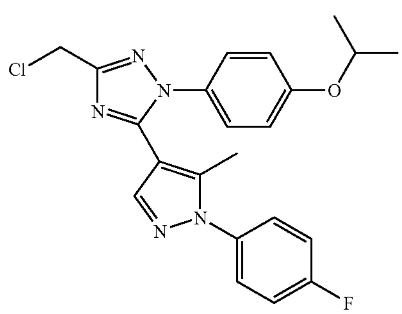 | MS calculated for $C_{22}H_{22}ClFN_5O$ (M + H$^+$) 426.1, found 426.2 |
| 19k | 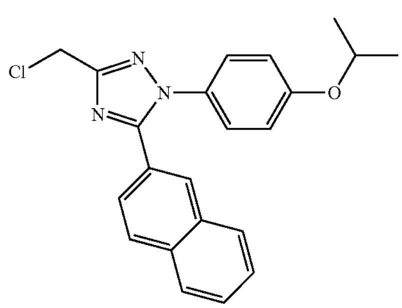 | MS calculated for $C_{22}H_{21}ClN_3O$ (M + H$^+$) 378.1, found 378.1 |

-continued

| Compound | Structure | Physical Data |
|---|---|---|
| 19l | 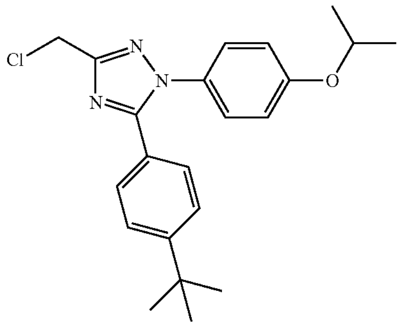 | MS calculated for C$_{22}$H$_{27}$ClN$_3$O (M + H$^+$) 384.2, found 384.1 |
| 19m | 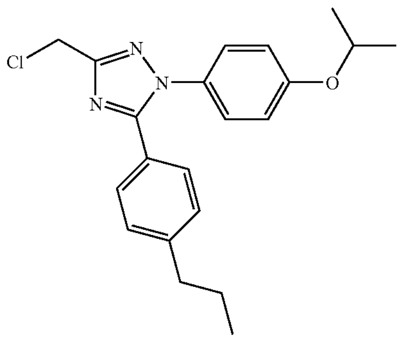 | MS calculated for C$_{21}$H$_{25}$ClN$_3$O (M + H$^+$) 370.2, found 370.2 |
| 19n | 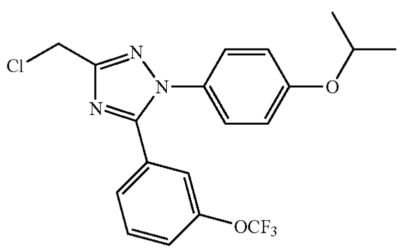 | MS calculated for C$_{19}$H$_{18}$ClF$_3$N$_3$O$_2$ (M + H$^+$) 412.1, found 412.1 |
| 19o | 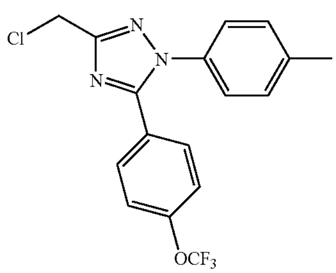 | MS calculated for C$_{17}$H$_{14}$ClF$_3$N$_3$O (M + H$^+$) 368.1, found 368.1 |
| 19p | 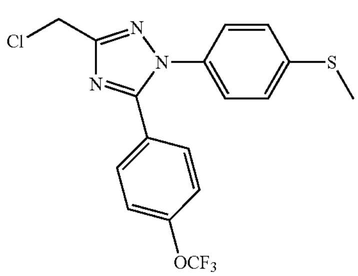 | MS calculated for C$_{17}$H$_{14}$ClF$_3$N$_3$OS (M + H$^+$) 400.0, found 400.0 |

| Compound | Structure | Physical Data |
|---|---|---|
| 19q | 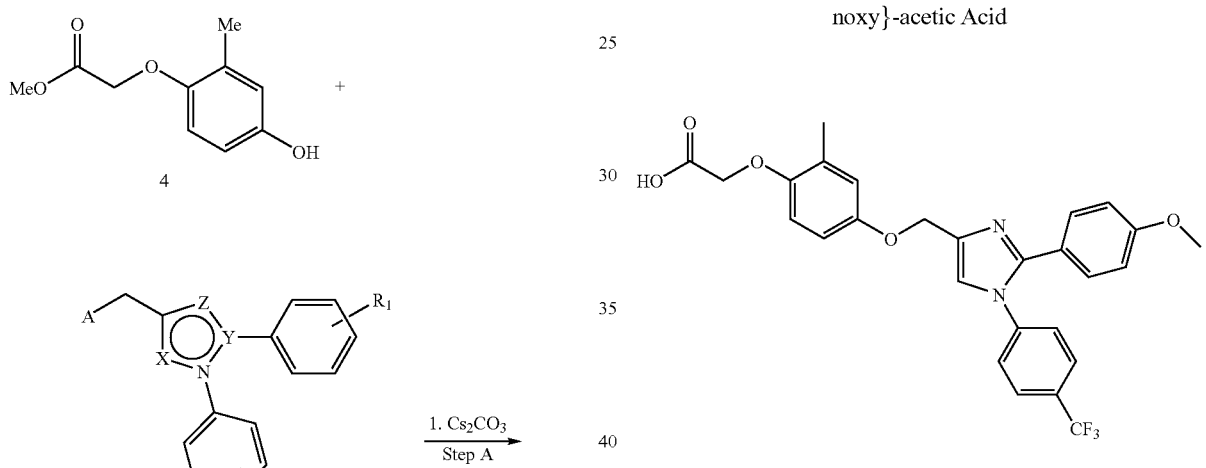 | MS calculated for $C_{17}H_{11}ClF_6N_3O$ (M + H⁺) 422.0, found 422.0 |

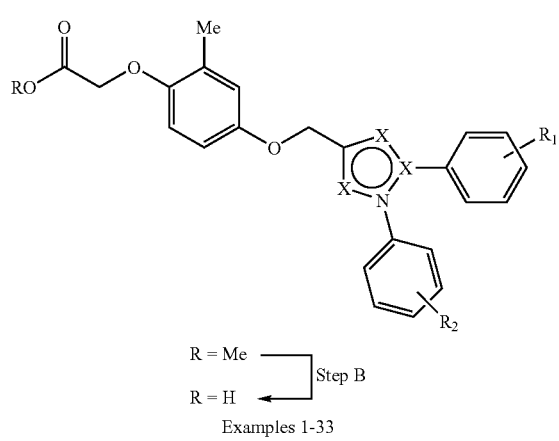

11 a-j X = Y = CH, Z = N, A = Cl
15 a-q X = N, Y = Z = CH, A = Cl or SO₂Me
19 a-f X = Z = N, Y = CH, A = Cl

R = Me ⎤
        ⎥ Step B
R = H  ⎦

Examples 1-33

Example 1

{4-[2-(4-Methoxy-phenyl)-1-(4-trifluoromethyl-phenyl)-1H-imidazol-4-ylmethoxy]-2-methyl-phenoxy}-acetic Acid Step A: 2-(4-hydroxy-phenoxy)-propionic acid methyl ester 4 (54 mg, 0.27 mmol) and Cs₂CO₃ (269 mg, 0.825 mmol) are added to a solution of intermediate 11a (92 mg, 0.25 mmol) in MeCN (5 mL). The mixture is stirred for 3 hours at room temperature. After the mixture is filtered, the organic solution is concentrated to afford crude {4-[2-(4-Methoxy-phenyl)-1-(4-trifluoromethyl-phenyl)-1H-imidazol-4-ylmethoxy]-2-methyl-phenoxy}-acetic acid methyl ester, which is used in the next step without further purification.

Step B: THF (2 mL) and 1 N LiOH (0.5 mL) are added to the crude product from step B. The mixture is heated at 70° C. and stirred for 2 hours, then acidified with 1 N HCl (1 mL). The reaction mixture is extracted with EtOAc (3 mL), the organic layer is separated and concentrated in vacuo. The remainder is taken up in DMSO (1 mL) and purified on reverse phase HPLC (H₂O/MeCN gradient) to afford the title compound 1 (36 mg, 0.07 mmol, 28%) as a white solid: ¹H-NMR (400 MHz, CDCl₃) δ=7.72 (d, J=8.0 Hz, 1H), 7.57 (m, 2H), 7.40 (d, J=8.4 Hz, 1H), 7.31 (d, J=8.4 Hz, 2H), 7.25 (s, 1H), 6.84 (d, J=8.8 Hz, 2H), 6.80 (s, 1H), 6.64 (d, J=8.4 Hz, 1H), 6.58 (d, J=8.8 Hz, 1H), 5.08 (s, 2H), 4.50 (s, 2H), 3.80 (s, 3H), 2.2 (s, 3H); MS calculated for $C_{27}H_{24}F_3N_2O_5$ (M+H⁺) 512.2, found 512.1.

Example 2

{4-[1-(6-Methoxy-pyridin-3-yl)-5-(4-trifluoromethoxy-phenyl)-1H-pyrazol-3-ylmethoxy]-2-methyl-phenoxy}-acetic Acid

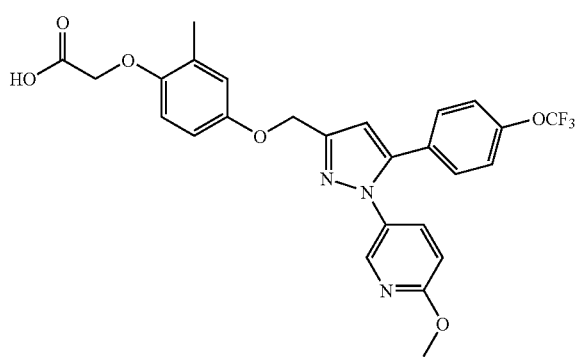

Step A: 2-(4-hydroxy-phenoxy)-propionic acid methyl ester 4 (273 mg, 1.39 mmol) and $Cs_2CO_3$ (828 mg, 2.54 mmol) are added to a solution of intermediate 15a (485 mg, 1.27 mmol) in MeCN (40 mL). The mixture is heated at reflux for 3 hours.

Step B: 1 N LiOH (5 mL) is added directly to the reaction mixture from Step A, and the mixture is heated at 80° C. for 2 hours, then cooled and acidified with 1 N HCl (30 mL). The reaction mixture is extracted with EtOAc (2×50 mL), the organic layers are combined and concentrated in vacuo. The remainder is taken up in DMSO (6 mL) and purified on reverse phase HPLC ($H_2O$/MeCN gradient) to afford the title compound 2 as a white solid: $^1$H-NMR (400 MHz, $CDCl_3$) δ=8.01 (d, J=2.4 Hz, 1H), 7.47 (dd, J=2.8, 8.8 Hz, 1H), 7.19 (d, J=8.8 Hz, 2H), 7.10 (d, J=8.4 Hz, 2H), 6.82 (d, J=2.8 Hz, 1H), 6.74 (dd, J=2.8, 8.8 Hz, 1H), 6.69 (d, J=8.8 Hz, 1H), 6.64 (d, J=8.8 Hz, 1H), 6.55 (s, 1H), 5.04 (s, 2H), 4.55 (s, 2H), 3.88 (s, 3H), 2.21 (s, 3H); MS calculated for $C_{26}H_{23}F_3N_3O_6$ (M+H$^+$) 530.2, found 530.1.

Example 3

{4-[1-(4-Isopropoxy-phenyl)-5-(4-trifluoromethoxy-phenyl)-1H-[1,2,4]triazol-3-ylmethoxy]-2-methyl-phenoxy}-acetic Acid

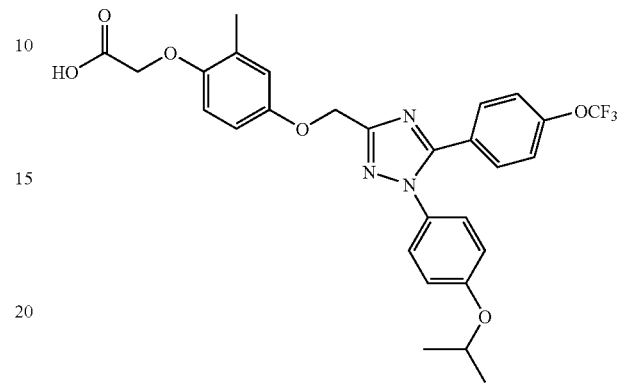

Step A: 2-(4-hydroxy-phenoxy)-propionic acid methyl ester 4 (477 mg, 2.43 mmol) and $Cs_2CO_3$ (1.6 g, 4.86 mmol) are added to a solution of intermediate 19a (1 g, 2.43 mmol) in MeCN (50 mL). The mixture is heated at reflux for 3 hours.

Step B: 1 N LiOH (10 mL) is added directly to the reaction mixture from Step A, and the mixture is heated at 80° C. for 2 hours, then cooled and acidified with 1 N HCl (50 mL). The reaction mixture is extracted with EtOAc (2×100 mL), the organic layers are combined and concentrated in vacuo. The remainder is taken up in DMSO (6 mL) and purified on reverse phase HPLC ($H_2O$/MeCN gradient) to afford the title compound as a white solid: $^1$H-NMR (400 MHz, $CDCl_3$) δ=7.57 (d, J=8.8 Hz, 2H), 7.24 (d, J=9.2 Hz, 2H), 7.19 (d, J=8.0 Hz, 2H), 6.93 (m, 3H), 6.79 (dd, J=2.8, 8.8 Hz, 1H), 6.65 (d, J=8.8 Hz, 1H), 5.17 (s, 2H), 4.58 (m, 3H), 2.27 (s, 3H), 1.38 (s, 3H), 1.36 (s, 3H); MS calculated for $C_{28}H_{27}F_3N_3O_6$ (M+H$^+$) 558.2, found 558.2.

By repeating the procedures described in the above examples, using appropriate starting materials, the following compounds of Formula I, as identified in Table 1, are obtained.

TABLE 1

| Compound Number | Compound Structure | Physical Data $^1$H NMR 400 MHz (DMSO-$d_6$) and/or MS (m/z) |
|---|---|---|
| 4 | 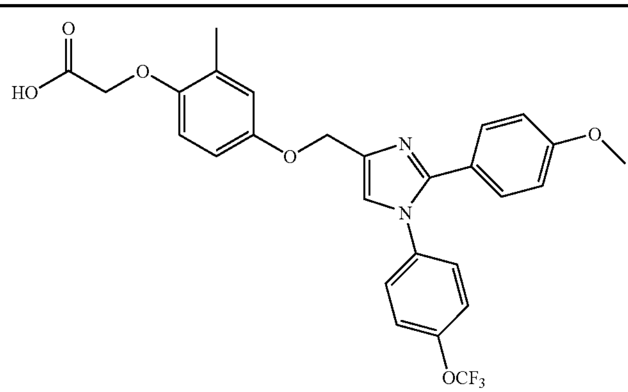 | $^1$H-NMR (400 MHz, $CDCl_3$) δ = 7.53(d, J = 8.8 Hz, 2 H), 7.48(m, 4 H), 7.40(s, 1 H), 7.04(d, J = 8.4 Hz, 2 H), 6.99(s, 1 H), 6.83 (d, J = 8.8 Hz, 1 H), 6.77(d, J = 8.8 Hz, 1 H), 5.27(s, 2 H), 4.69(s, 2 H), 4.00(s, 3 H), 2.39(s, 3 H). MS calculated for $C_{27}H_{24}F_3N_2O_6$ (M + H$^+$) 529.2, found 529.1. |

TABLE 1-continued

| Compound Number | Compound Structure | Physical Data $^1$H NMR 400 MHz (DMSO-$d_6$) and/or MS (m/z) |
|---|---|---|
| 5 | 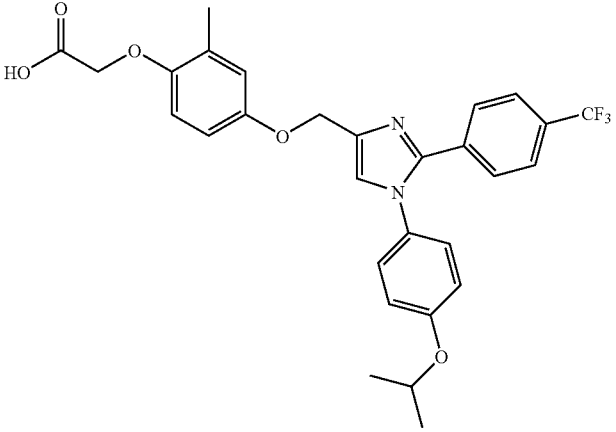 | $^1$H-NMR (400 MHz, CDCl$_3$) δ = 7.49(s, 4 H), 7.19(s, 1 H), 7.04(d, J = 8.8 Hz, 2 H), 6.83(d, J = 8.8 Hz, 2 H), 6.77(d, J = 2.4 Hz, 1 H), 6.61(dd, J = 2.8, 8.8 Hz, 1 H), 6.54(d, J = 8.8 Hz, 1 H), 5.01(s, 2 H), 4.50 (m, 1 H), 4.44(s, 2 H), 2.18(s, 3 H), 1.31(s, 3 H), 1.29(s, 3 H). MS calculated for C$_{29}$H$_{28}$F$_3$N$_2$O$_5$ (M + H$^+$) 541.2, found 541.1. |
| 6 | 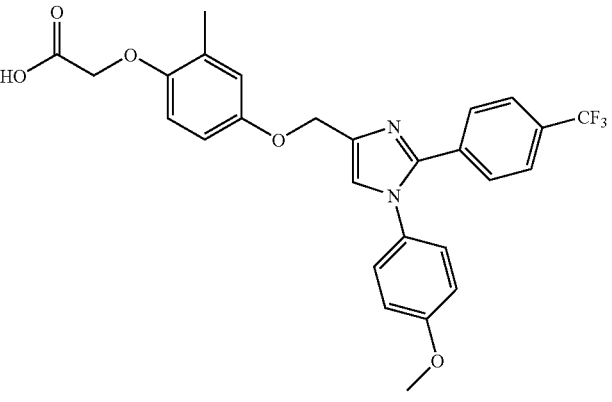 | $^1$H-NMR (400 MHz, CDCl$_3$) δ = 7.59(m, 4 H), 7.27(s, 1 H), 7.17(d, J = 8.8 Hz, 2 H), 6.96(d, J = 8.8 Hz, 2 H), 6.83(d, J = 2.8 Hz, 1 H), 6.71(dd, J = 2.8, 8.8 Hz, 1 H), 6.64(d, J = 8.8 Hz, 1 H), 5.16(s, 2 H), 4.55 (s, 2 H), 3.84(s, 3 H), 2.24(s, 3 H). MS calculated for C$_{27}$H$_{25}$F$_3$N$_2$O$_5$ (M + H$^+$) 513.2, found 513.1. |
| 7 | 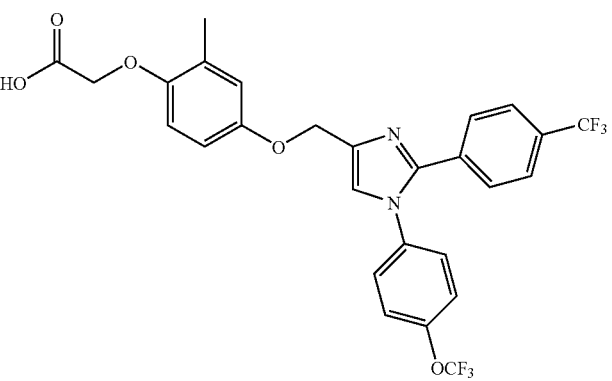 | $^1$H-NMR (400 MHz, CDCl$_3$) δ = 7.57(d, J = 8.4 Hz, 2 H), 7.52(d, J = 8.4 Hz, 2 H), 7.32 (m, 4 H), 6.85(d, J = 2.8 Hz, 1 H), 6.70(dd, J = 2.8, 8.8 Hz, 1 H), 6.63(d, J = 8.8 Hz, 1 H), 5.08(s, 2 H), 4.54(s, 2 H), 3.84(s, 3 H), 2.25(s, 3 H). MS calculated for C$_{27}$H$_{21}$F$_6$N$_2$O$_5$ (M + H$^+$) 567.1, found 567.1. |

TABLE 1-continued

| Compound Number | Compound Structure | Physical Data<br>$^1$H NMR 400 MHz (DMSO-$d_6$) and/or MS (m/z) |
|---|---|---|
| 8 | 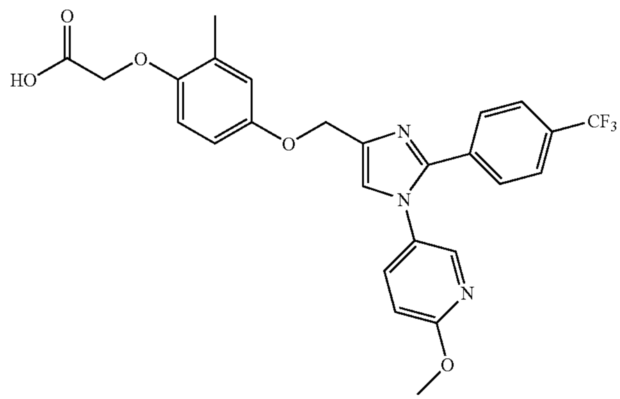 | $^1$H-NMR (400 MHz, CDCl$_3$) δ = 8.12(d, J = 2.4 Hz, 1 H), 7.60(d, J = 8.4 Hz, 2 H), 7.55 (d, J = 8.4 Hz, 2 H), 7.23(s, 1 H), 6.85(d, J = 2.8 Hz, 1 H), 6.71(dd, J = 2.8, 8.8 Hz, 1 H), 6.64(d, J = 8.8 Hz, 1 H), 5.11(s, 2 H), 4.55(s, 2 H), 3.98(s, 3 H), 2.25(s, 3 H). MS calculated for C$_{26}$H$_{23}$F$_3$N$_3$O$_5$ (M + H$^+$) 513.2, found 513.2. |
| 9 | 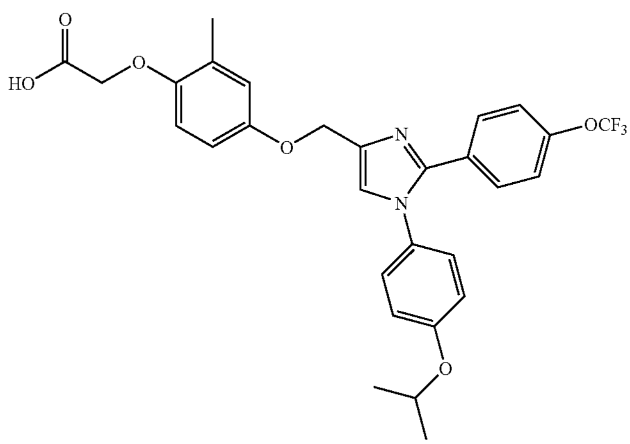 | $^1$H-NMR (400 MHz, CDCl$_3$) δ = 7.40(d, J = 8.8 Hz, 2 H), 7.11(s, 1 H), 7.05(m, 4 H), 6.83(d, J = 8.8 Hz, 2 H), 6.77(d, J = 2.8 Hz, 1 H), 6.61(dd, J = 2.8, 9.2 Hz, 1 H), 6.55(d, J = 9.2 Hz, 1 H), 4.99(s, 2 H), 4.50 (m, 1 H), 4.43(s, 2 H), 2.18(s, 3 H), 1.30(s, 3 H), 1.29(s, 3 H). MS calculated for C$_{29}$H$_{28}$F$_3$N$_2$O$_6$ (M + H$^+$) 557.2, found 557.2. |
| 10 | 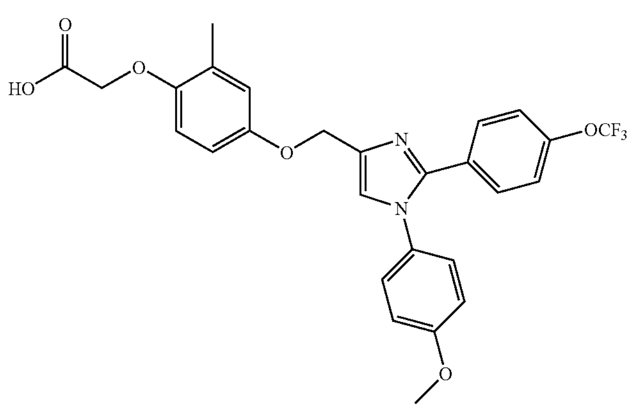 | $^1$H-NMR (400 MHz, CDCl$_3$) δ = 7.35(d, J = 8.8 Hz, 2 H), 7.10(d, J = 8.8 Hz, 2 H), 7.03 (m, 4 H), 6.81(d, J = 8.8 Hz, 2 H), 6.66(d, J = 2.8 Hz, 1 H), 6.52(dd, J = 3.2, 8.8 Hz, 1 H), 6.45(d, J = 8.8 Hz, 1 H), 4.99(s, 2 H), 4.36(s, 2 H), 3.71(s, 3 H), 2.06(s, 3 H). MS calculated for C$_{27}$H$_{24}$F$_3$N$_2$O$_6$ (M + H$^+$) 529.2, found 529.1. |

TABLE 1-continued

| Compound Number | Compound Structure | Physical Data $^1$H NMR 400 MHz (DMSO-d$_6$) and/or MS (m/z) |
|---|---|---|
| 11 | 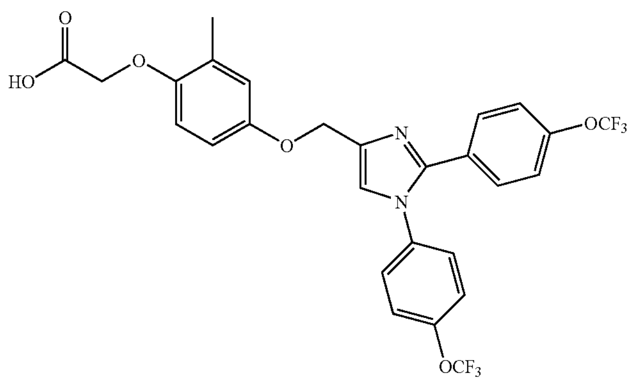 | $^1$H-NMR (400 MHz, CDCl$_3$) δ = 7.65(d, J = 8.8 Hz, 2 H), 7.50(m, 5 H), 7.36(d, J = 8.0 Hz, 2 H), 7.06(d, J = 2.8 Hz, 1 H), 6.89(dd, J = 2.8, 8.8 Hz, 1 H), 6.83(d, J = 8.8 Hz, 1 H), 5.27(s, 2 H), 4.73(s, 2 H), 2.46(s, 3 H). MS calculated for C$_{27}$H$_{21}$F$_6$N$_2$O$_6$ (M + H$^+$) 583.1, found 583.1. |
| 12 | 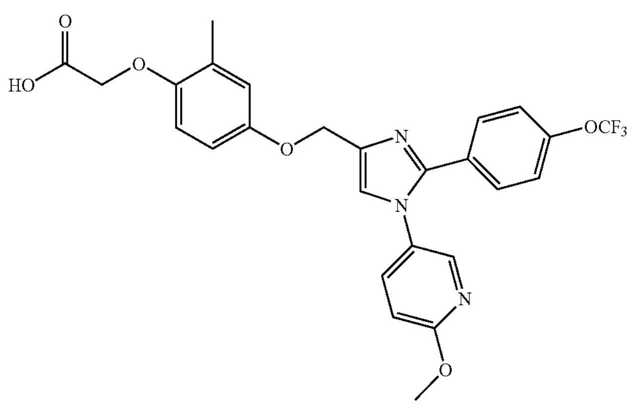 | $^1$H-NMR (400 MHz, CDCl$_3$) δ = 8.15(d, J = 2.4 Hz, 1 H), 7.51(d, J = 8.8 Hz, 2 H), 7.43 (dd, J = 2.8, 8.8 Hz, 1 H), 7.23(s, 1 H), 7.20 (d, J = 8.8 Hz, 2 H), 6.88(d, J = 2.8 Hz, 1 H), 6.83(d, J = 8.8 Hz, 1 H), 6.72(dd, J = 2.8, 8.8 Hz, 1 H), 6.66(d, J = 8.8 Hz, 1 H), 5.11(s, 2 H), 4.56(s, 2 H), 4.02(s, 3 H), 2.29 (s, 3 H). MS calculated for C$_{26}$H$_{23}$F$_3$N$_3$O$_6$ (M + H$^+$) 530.2, found 530.1. |
| 13 | 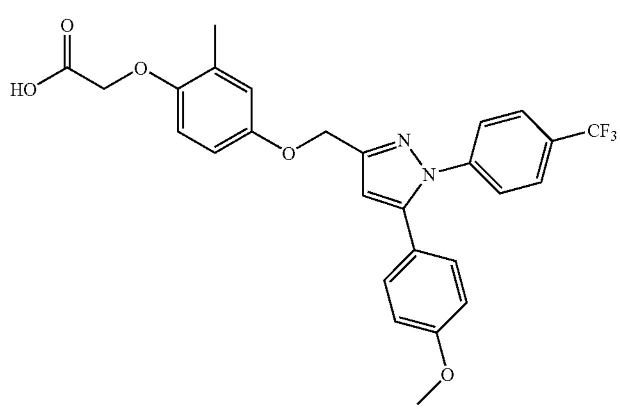 | $^1$H-NMR (400 MHz, CDCl$_3$) δ = 7.59(d, J = 8.4 Hz, 2 H), 7.43(d, J = 8.4 Hz, 2 H), 7.15 (d, J = 8.8 Hz, 2 H), 6.90(d, J = 2.8 Hz, 1 H), 6.86(d, J = 8.8 Hz, 2 H), 6.80(dd, J = 2.8, 8.8 Hz, 1 H), 6.70(d, J = 8.8 Hz, 1 H), 6.58(s, 1 H), 5.11(s, 2 H), 4.62(s, 2 H), 3.82 (s, 3 H), 2.29(s, 3 H). MS calculated for C$_{27}$H$_{24}$F$_3$N$_2$O$_5$ (M + H$^+$) 513.2, found 513.1. |

TABLE 1-continued

| Compound Number | Compound Structure | Physical Data<br>$^1$H NMR 400 MHz (DMSO-$d_6$) and/or MS (m/z) |
| --- | --- | --- |
| 14 | 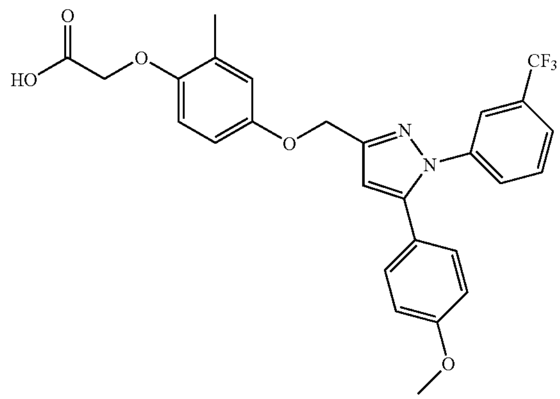 | $^1$H-NMR (400 MHz, CDCl$_3$) δ = 7.72(s, 1 H), 7.61(d, J = 7.2 Hz, 1 H), 7.49(d, J = 8.4 Hz, 1 H), 7.46(d, J = 2.0 Hz, 1 H), 7.18 (d, J = 8.8 Hz, 2 H), 6.95(d, J = 3.2 Hz, 1 H), 6.89(d, J = 8.8 Hz, 2 H), 6.86(dd, J = 2.8, 8.8 Hz, 1 H), 6.76(d, J = 8.8 Hz, 1 H), 6.63(s, 1 H), 5.17(s, 2 H), 4.68(s, 2 H), 3.86 (s, 3 H), 2.33(s, 3 H). MS calculated for C$_{27}$H$_{24}$F$_3$N$_2$O$_5$ (M + H$^+$) 513.2, found 513.1. |
| 15 | 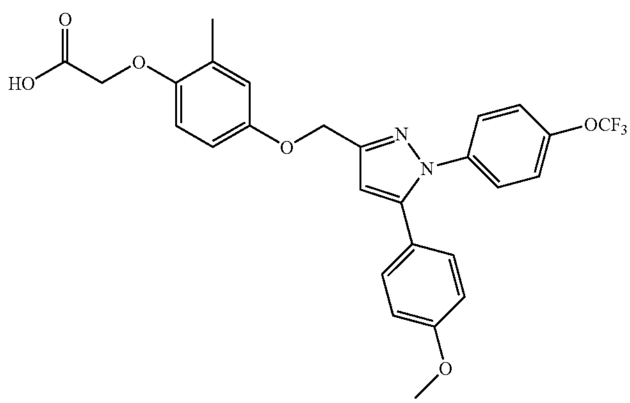 | $^1$H-NMR (400 MHz, CDCl$_3$) δ = 7.39(d, J = 8.8 Hz, 2 H), 7.24(d, J = 8.4 Hz, 2 H), 7.19 (d, J = 8.8 Hz, 2 H), 6.94(d, J = 2.8 Hz, 1 H), 6.90(d, J = 8.8 Hz, 2 H), 6.86(dd, J = 2.8, 8.8 Hz, 1 H), 6.76(d, J = 8.8 Hz, 1 H), 6.62(s, 1 H), 5.16(s, 2 H), 4.68(s, 2 H), 3.87 (s, 3 H), 2.33(s, 3 H). MS calculated for C$_{27}$H$_{24}$F$_3$N$_2$O$_6$ (M + H$^+$) 529.2, found 529.1. |
| 16 | 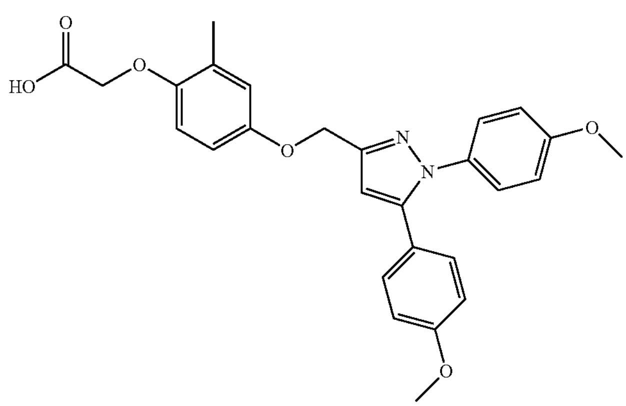 | $^1$H-NMR (400 MHz, CDCl$_3$) δ = 7.00(d, J = 8.8 Hz, 2 H), 6.92(d, J = 8.8 Hz, 2 H), 6.68 (d, J = 2.8 Hz, 1 H), 6.64(d, J = 8.8 Hz, 2 H), 6.60(d, J = 8.8 Hz, 2 H), 6.57(dd, J = 2.8, 8.8 Hz, 1 H), 6.47(d, J = 8.8 Hz, 1 H), 6.33(s, 1 H), 4.88(s, 2 H), 4.38(s, 2 H), 3.60 (s, 3 H), 3.58(s, 3 H), 2.06(s, 3 H). MS calculated for C$_{27}$H$_{27}$N$_2$O$_6$ (M + H$^+$) 475.2, found 475.1. |

TABLE 1-continued

| Compound Number | Compound Structure | Physical Data $^1$H NMR 400 MHz (DMSO-$d_6$) and/or MS (m/z) |
|---|---|---|
| 17 | 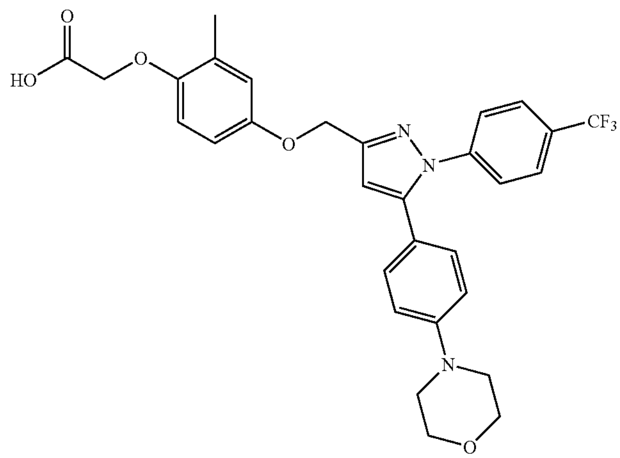 | $^1$H-NMR (400 MHz, CDCl$_3$) δ = 7.60(d, J = 8.8 Hz, 2 H), 7.44(d, J = 8.4 Hz, 2 H), 7.14 (d, J = 8.8 Hz, 2 H), 6.92(d, J = 8.8 Hz, 2 H), 6.88(d, J = 3.2 Hz, 1 H), 6.80(dd, J = 2.8, 8.8 Hz, 1 H), 6.70(d, J = 8.8 Hz, 1 H), 6.57(s, 1 H), 5.10(s, 2 H), 4.62(s, 2 H), 3.90 (m, 4 H), 3.24(m, 4 H), 2.28(s, 3 H). MS calculated for C$_{30}$H$_{29}$F$_3$N$_3$O$_5$ (M + H$^+$) 568.2, found 568.2. |
| 18 | 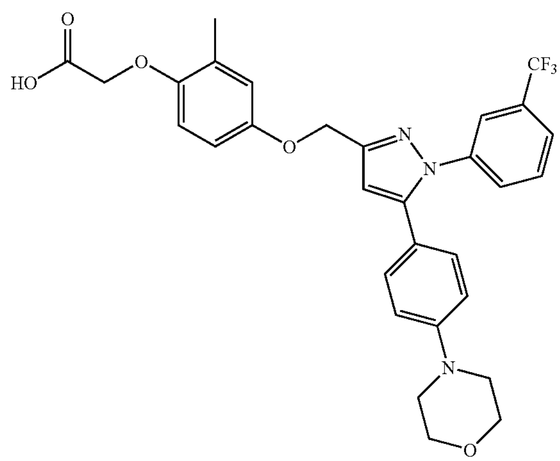 | $^1$H-NMR (400 MHz, CDCl$_3$) δ = 7.67(s, 1 H), 7.55(m, 1 H), 7.43(m, 2 H), 7.13(d, J = 8.8 Hz, 2 H), 6.91(d, J = 8.8 Hz, 2 H), 6.90(d, J = 2.8 Hz, 1 H), 6.80(dd, J = 2.8, 8.8 Hz, 1 H), 6.70(d, J = 8.8 Hz, 1 H), 6.57 (s, 1 H), 5.11(s, 2 H), 4.62(s, 2 H), 3.90(m, 4 H), 3.22(m, 4 H), 2.28(s, 3 H). MS calculated for C$_{30}$H$_{29}$F$_3$N$_3$O$_5$ (M + H$^+$) 568.2, found 568.2. |
| 19 | 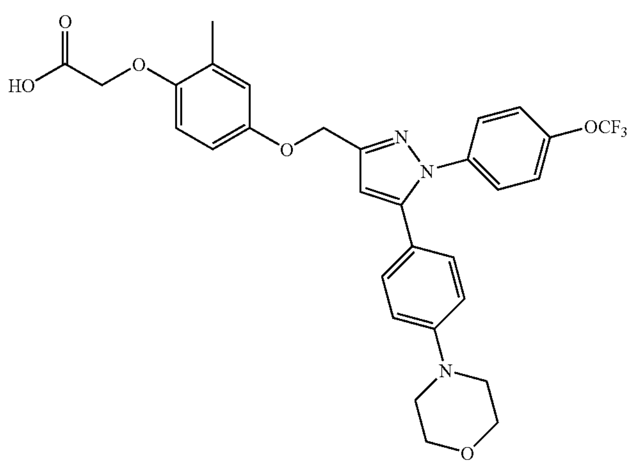 | $^1$H-NMR (400 MHz, CD$_3$CN) δ = 7.16(d, J = 8.8 Hz, 2 H), 7.08(d, J = 8.4 Hz, 2 H), 6.93(d, J = 8.8 Hz, 2 H), 6.80(m, 3 H), 6.61 (dd, J = 2.8, 8.8 Hz, 1 H), 6.54(d, J = 8.8 Hz, 1 H), 6.37(s, 1 H), 4.84(s, 2 H), 4.40(s, 2 H), 3.57(m, 4 H), 2.95(m, 4 H), 2.02(s, 3 H). MS calculated for C$_{30}$H$_{29}$F$_3$N$_3$O$_6$ (M + H$^+$) 584.2, found 584.2. |

TABLE 1-continued

| Compound Number | Compound Structure | Physical Data <sup>1</sup>H NMR 400 MHz (DMSO-d<sub>6</sub>) and/or MS (m/z) |
|---|---|---|
| 20 | 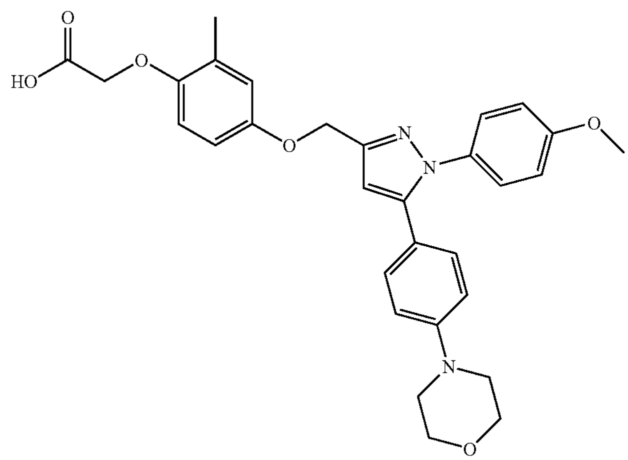 | $^1$H-NMR (400 MHz, CDCl$_3$) δ = 7.23(d, J = 8.8 Hz, 2 H), 7.13(d, J = 8.8 Hz, 2 H), 6.86 (m, 5 H), 6.79(dd, J = 3.2, 8.8 Hz, 1 H), 6.68(d, J = 8.8 Hz, 1 H), 6.54(s, 1 H), 5.09 (s, 2 H), 4.60(s, 2 H), 3.89(m, 4 H), 3.20(m, 4 H), 2.27(s, 3 H). MS calculated for C$_{30}$H$_{32}$N$_3$O$_6$ (M + H$^+$) 530.2, found 530.2. |
| 21 | 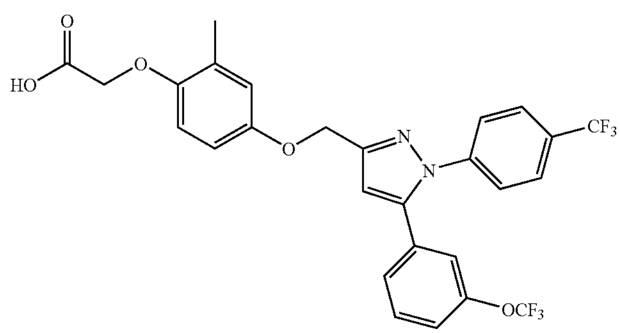 | $^1$H-NMR (400 MHz, CDCl$_3$) δ = 7.63(d, J = 8.4 Hz, 2 H), 7.40(m, 3 H), 7.21(dd, J = 1.2, 8.8 Hz, 1 H), 7.18(d, J = 9.2 Hz, 1H), 7.05(s, 1 H), 6.89(d, J = 2.8 Hz, 1 H), 6.81 (dd, J = 2.8, 8.8 Hz, 1 H), 6.71(d, J = 8.8 Hz, 1 H), 6.69(s, 1 H), 5.13(s, 2 H), 4.64(s, 2 H), 2.29(s, 3 H). MS calculated for C$_{27}$H$_{21}$F$_6$N$_2$O$_5$ (M + H$^+$) 567.1, found 567.1. |
| 22 | 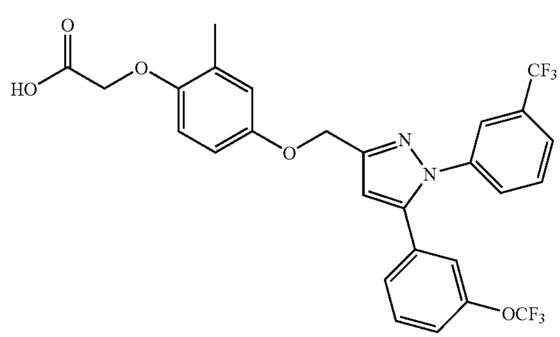 | $^1$H-NMR (400 MHz, CDCl$_3$) δ = 7.60(d, J = 6.8 Hz, 2 H), 7.49(t, J = 8.4 Hz, 1 H), 7.43 (d, J = 8.8 Hz, 1 H), 7.39(t, J = 8.0 Hz, 1 H), 7.20(m, 2 H), 7.03(s, 1 H), 6.89(d, J = 2.8 Hz, 1 H), 6.81(dd, J = 2.8, 8.8 Hz, 1 H), 6.71(d, J = 8.8 Hz, 1 H), 6.69(s, 1 H), 5.14 (s, 2 H), 4.64(s, 2 H), 2.29(s, 3 H). MS calculated for C$_{27}$H$_{21}$F$_6$N$_2$O$_5$ (M + H$^+$) 567.1, found 567.1. |
| 23 | 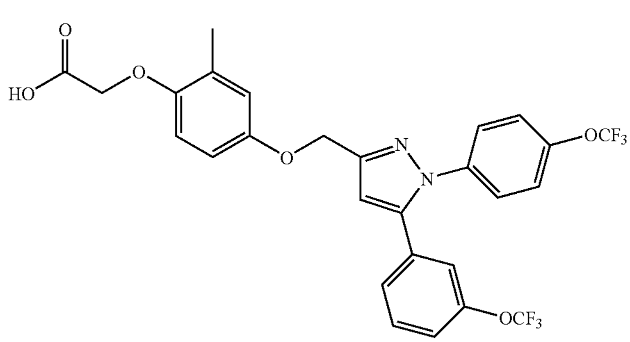 | $^1$H-NMR (400 MHz, CDCl$_3$) δ = 7.38(t, J = 8.0 Hz, 1 H), 7.32(d, J = 8.8 Hz, 1 H), 7.21 (m, 4 H), 7.01(s, 1 H), 6.89(d, J = 2.8 Hz, 1 H), 6.81(dd, J = 2.8, 8.8 Hz, 1 H), 6.71(d, J = 8.8 Hz, 1 H), 6.67(s, 1 H), 5.12(s, 2 H), 4.63(s, 2 H), 2.29(s, 3 H). MS calculated for C$_{27}$H$_{20}$F$_6$N$_2$O$_6$ (M + H$^+$) 583.1, found 583.1. |

TABLE 1-continued

| Compound Number | Compound Structure | Physical Data $^1$H NMR 400 MHz (DMSO-$d_6$) and/or MS (m/z) |
|---|---|---|
| 24 | 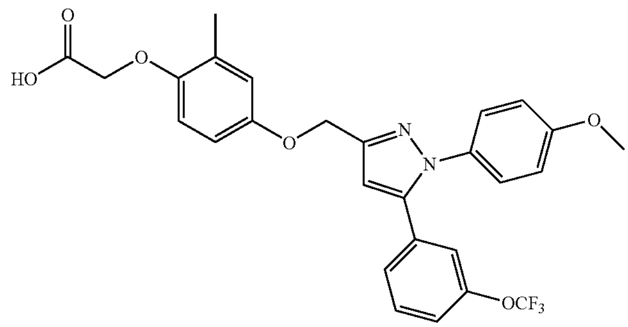 | $^1$H-NMR (400 MHz, CD$_3$CN) δ = 7.56(t, J = 8.0 Hz, 1 H), 7.43(d, J = 8.0 Hz, 1 H), 7.39(d, J = 8.4 Hz, 1 H), 7.35(d, J = 8.8 Hz, 2 H), 7.24(s, 1 H), 7.08(d, J = 8.8 Hz, 2 H), 7.04(d, J = 2.8 Hz, 1 H), 6.96(dd, J = 2.8, 8.8 Hz, 1 H), 6.90(d, J = 8.8 Hz, 1 H), 6.85(s, 1 H), 5.20(s, 2 H), 4.75(s, 2 H), 3.94 (s, 3 H), 2.37(s, 3 H). MS calculated for C$_{27}$H$_{24}$F$_3$N$_2$O$_6$ (M + H$^+$) 529.2, found 529.1. |
| 25 | 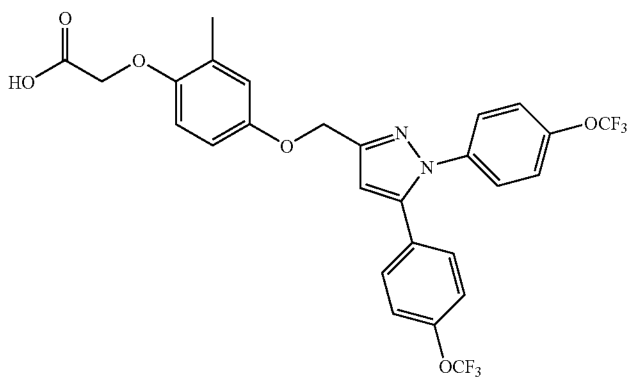 | $^1$H-NMR (400 MHz, CDCl$_3$) δ = 7.49(d, J = 8.8 Hz, 2 H), 7.41(d, J = 8.4 Hz, 2 H), 7.38 (d, J = 8.4 Hz, 2 H), 7.34(d, J = 8.4 Hz, 2 H), 7.05(d, J = 2.8 Hz, 1 H), 6.97(dd, J = 3.2, 8.8 Hz, 1 H), 6.87(d, J = 8.8 Hz, 1 H), 6.80(s, 1 H), 5.28(s, 2 H), 4.80(s, 2 H), 2.45 (s, 3 H). MS calculated for C$_{27}$H$_{21}$F$_6$N$_2$O$_6$ (M + H$^+$) 583.1, found 583.2. |
| 26 | 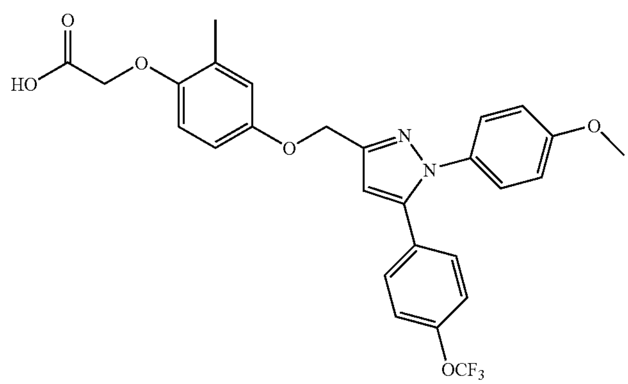 | $^1$H-NMR (400 MHz, CDCl$_3$) δ = 7.24(d, J = 8.8 Hz, 2 H), 7.20(d, J = 8.8 Hz, 2 H), 7.13 (d, J = 8.4 Hz, 2 H), 6.88(m, 3 H), 6.79(dd, J = 3.2, 8.8 Hz, 1 H), 6.69(d, J = 8.8 Hz, 1 H), 6.61(s, 1 H), 5.10(s, 2 H), 4.61(s, 2 H), 3.83(s, 3 H), 2.28(s, 3 H). MS calculated for C$_{27}$H$_{24}$F$_3$N$_2$O$_6$ (M + H$^+$) 529.2, found 529.2. |
| 27 | 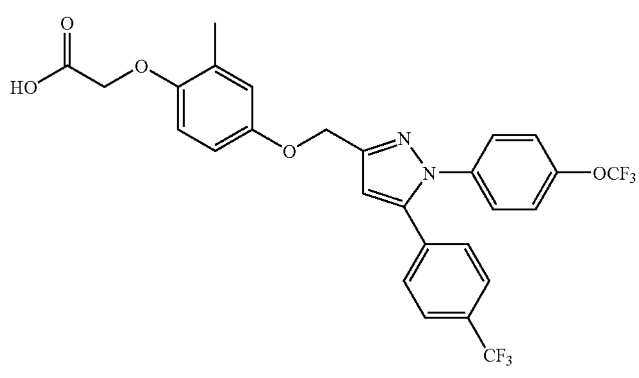 | $^1$H-NMR (400 MHz, CDCl$_3$) δ = 7.59(d, J = 8.0 Hz, 2 H), 7.33(m, 4 H), 7.22(d, J = 8.4 Hz, 2 H), 6.89(d, J = 2.8 Hz, 1 H), 6.81(dd, J = 3.2, 8.8 Hz, 1 H), 6.71(d, J = 8.8 Hz, 1 H), 6.69(s, 1 H), 5.12(s, 2 H), 4.64(s, 2 H), 2.28(s, 3 H). MS calculated for C$_{27}$H$_{21}$F$_6$N$_2$O$_5$(M + H$^+$) 567.1, found 567.1. |

TABLE 1-continued

| Compound Number | Compound Structure | Physical Data $^1$H NMR 400 MHz (DMSO-d$_6$) and/or MS (m/z) |
|---|---|---|
| 28 | 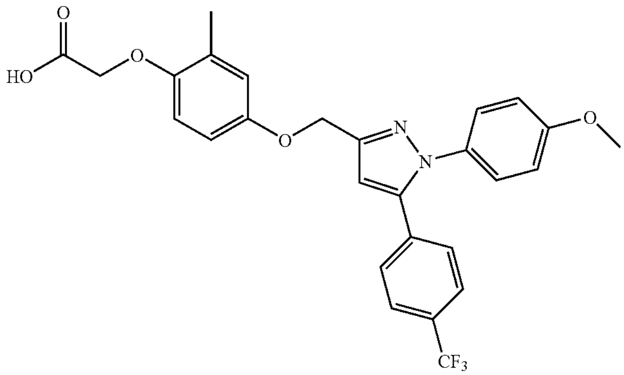 | $^1$H-NMR (400 MHz, CDCl$_3$) δ = 7.55(d, J = 8.0 Hz, 2 H), 7.33(d, J = 8.4 Hz, 2 H), 7.20 (d, J = 8.8 Hz, 2 H), 6.88(m, 3 H), 6.80(dd, J = 2.8, 8.8 Hz, 1 H), 6.69(d, J = 8.8 Hz, 1 H), 6.67(s, 1 H), 5.12(s, 2 H), 4.62(s, 2 H), 3.83(s, 3 H), 2.28(s, 3 H). MS calculated for C$_{27}$H$_{23}$F$_3$N$_2$O$_5$ (M + H$^+$) 513.2, found 513.2. |
| 29 | 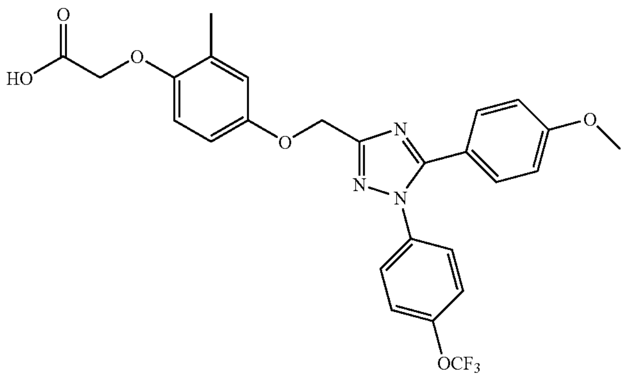 | $^1$H-NMR (400 MHz, CDCl$_3$) δ = 7.42(m, 4 H), 7.27(d, J = 9.2 Hz, 2 H), 6.89(m, 3 H), 6.74(dd, J = 2.8, 8.8 Hz, 1 H), 6.61(d, J = 8.8 Hz, 1 H), 5.16(s, 2 H), 4.55(s, 2 H), 3.82 (s, 3 H), 2.26(s, 3 H). MS calculated for C$_{26}$H$_{23}$F$_3$N$_3$O$_6$ (M + H$^+$) 530.2, found 530.1 |
| 30 | 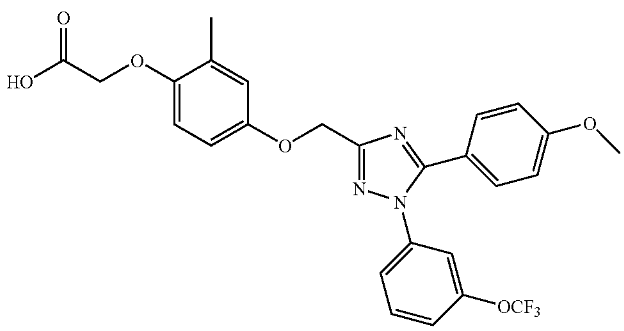 | $^1$H-NMR (400 MHz, CDCl$_3$) δ = 7.47(t, J = 8.0 Hz, 1 H), 7.42(d, J = 8.8 Hz, 2 H), 7.32 (m, 2 H), 6.92(d, J = 2.8 Hz, 1 H), 689(d, J = 8.8 Hz, 2 H), 6.77(dd, J = 2.8, 8.8 Hz, 1 H), 6.64(d, J = 8.8 Hz, 1 H), 5.17(s, 2 H), 4.58(s, 2 H), 3.84(s, 3 H), 2.27(s, 3 H). MS calculated for C$_{26}$H$_{23}$F$_3$N$_3$O$_6$ (M + H$^+$) 530.2, found 530.2 |
| 31 | 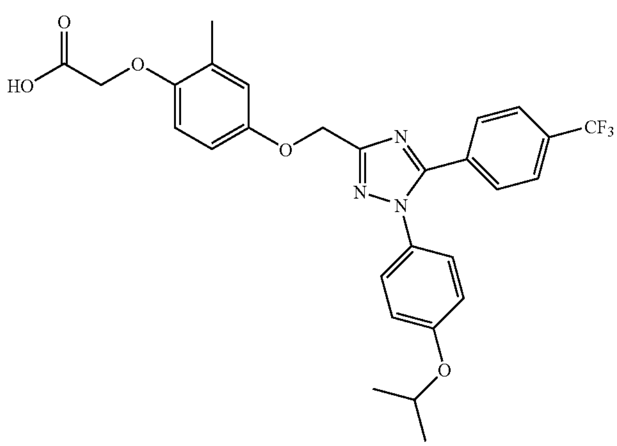 | $^1$H-NMR (400 MHz, CDCl$_3$) δ = 7.65(d, J = 8.8 Hz, 2 H), 7.61(d, J = 8.4 Hz, 2 H), 7.23 (d, J = 8.8 Hz, 2 H), 6.92(m, 3 H), 6.80(dd, J = 2.8, 8.8 Hz, 1 H), 6.66(d, J = 8.8 Hz, 1 H), 5.18(s, 2 H), 4.59(m, 3 H), 2.27(s, 3 H), 1.38(s, 3 H), 1.36(s, 3 H). MS calculated for C$_{28}$H$_{27}$F$_3$N$_3$O$_5$ (M + H$^+$) 542.2, found 542.2 |

TABLE 1-continued

| Compound Number | Compound Structure | Physical Data $^1$H NMR 400 MHz (DMSO-$d_6$) and/or MS (m/z) |
|---|---|---|
| 32 | 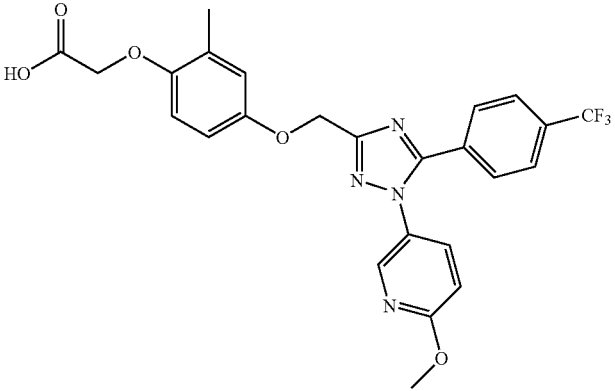 | $^1$H-NMR (400 MHz, CDCl$_3$) δ = 8.15(d, J = 2.8 Hz, 1 H), 7.66(s, 4 H), 7.59(dd, J = 2.4, 8.8 Hz, 1 H), 6.93(d, J = 2.8 Hz, 1 H), 6.84 (dd, J = 2.8, 8.8 Hz, 1 H), 6.69(d, J = 8.8 Hz, 1 H), 5.19(s, 2 H), 4.61(s, 2 H), 3.99(s, 3 H), 2.28(s, 3 H). MS calculated for C$_{25}$H$_{21}$F$_3$N$_4$O$_5$ (M + H$^+$) 515.2, found 515.1 |
| 33 | 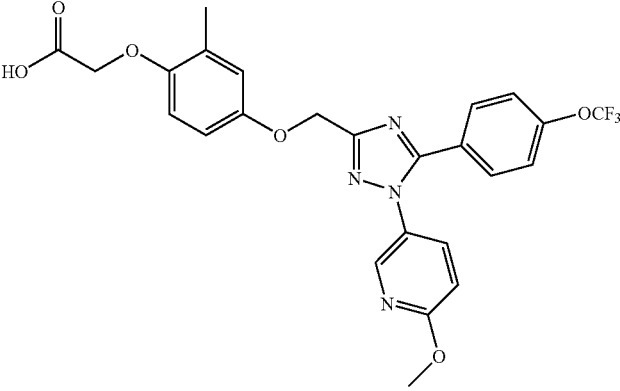 | $^1$H-NMR (400 MHz, CDCl$_3$) δ = 8.16(d, J = 2.4 Hz, 1 H), 7.58(m, 3 H), 7.22(d, J = 8.8 Hz, 2 H), 6.93(d, J = 2.8 Hz, 1 H), 6.83(dd, J = 3.2, 8.8 Hz, 1 H), 6.69(d, J = 8.8 Hz, 1 H), 5.17(s, 2 H), 4.61(s, 2 H), 3.99(s, 3 H), 2.28(s, 3 H). MS calculated for C$_{25}$H$_{22}$F$_3$N$_4$O$_6$ (M + H$^+$) 531.1, found 531.1 |
| 34 | 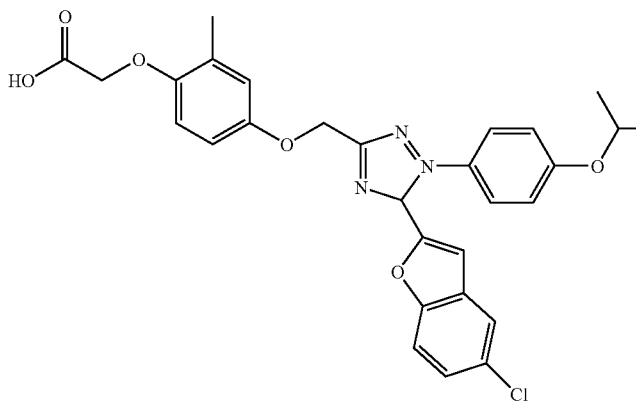 | $^1$H-NMR (400 MHz, CDCl$_3$) δ = 7.63(d, J = 2.0 Hz, 1 H), 7.50(m, 3 H), 7.41(dd, J = 2.0, 8.8 Hz, 1 H), 7.14(d, J = 8.8 Hz, 2 H), 7.04(d, J = 2.8 Hz, 1 H), 6.94(d, J = 2.8, 8.8 Hz, 1 H), 6.83(s, 1 H), 6.81(d, J = 8.8 Hz, 1 H), 5.31(s, 2 H), 4.76(m, 1 H), 4.72 (s, 2 H), 2.38(s, 3 H), 1.53(s, 3 H), 1.51(s, 3 H). MS calculated for C$_{29}$H$_{27}$ClN$_3$O$_6$ (M + H$^+$) 548.2, found 548.2 |

TABLE 1-continued

| Compound Number | Compound Structure | Physical Data $^1$H NMR 400 MHz (DMSO-$d_6$) and/or MS (m/z) |
|---|---|---|
| 35 | 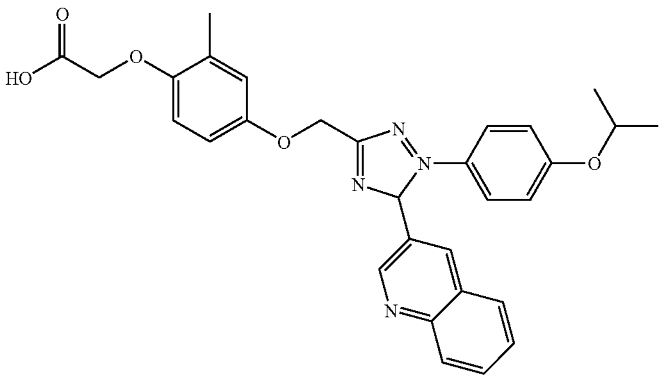 | $^1$H-NMR (400 MHz, CDCl$_3$) δ = 9.26(d, J = 2.0 Hz, 1 H), 8.82(d, J = 2.0 Hz, 1 H), 8.53 (d, J = 8.4 Hz, 1 H), 8.06(m, 2 H), 7.90(d, J = 7.6 Hz, 1 H), 7.47(d, J = 8.8 Hz, 2 H), 7.13(d, J = 8.8 Hz, 2 H), 7.10(d, J = 2.8 Hz, 1 H), 7.05(dd, J = 2.8, 8.8 Hz, 1 H), 6.88(d, J = 8.8 Hz, 1 H), 5.40(s, 2 H), 4.81 (s, 2 H), 4.77(m, 1 H), 2.43(s, 3 H), 1.55(s, 6 H). MS calculated for C$_{30}$H$_{29}$N$_4$O$_5$ (M + H$^+$) 525.2, found 525.3 |
| 36 | 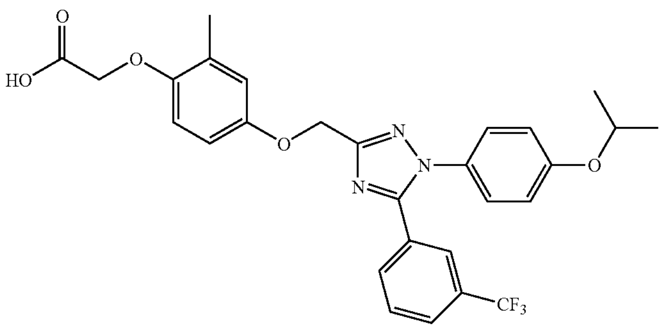 | $^1$H-NMR (400 MHz, CDCl$_3$) δ = 7.81(s, 1 H), 7.68(t, J = 8.8 Hz, 2 H), 7.48(t, J = 8.0 Hz, 1 H), 7.24(d, J = 8.4 Hz, 2 H), 6.93 (d, J = 8.8 Hz, 3 H), 6.80(dd, J = 2.8, 8.8 Hz, 1 H), 6.66(d, J = 8.8 Hz, 1 H), 5.19(s, 2 H), 4.58(m, 3 H), 2.27(s, 3 H), 1.36(s, 3 H), 1.35(s, 3 H). MS calculated for C$_{28}$H$_{27}$F$_3$N$_3$O$_5$ (M + H$^+$) 542.2, found 542.2 |
| 37 | 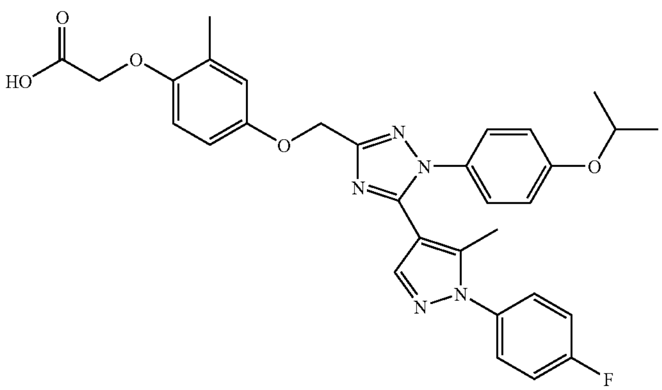 | $^1$H-NMR (400 MHz, CDCl$_3$) δ = 7.21(m, 2 H), 7.16(d, J = 8.8 Hz, 2 H), 7.06(s, 1 H), 7.01(t, J = 8.8 Hz, 2 H), 6.79(d, J = 8.8 Hz, 2 H), 6.76(d, J = 2.8 Hz, 1 H), 6.64(dd, J = 2.8, 8.8 Hz, 1 H), 6.47(d, J = 8.8 Hz, 1 H), 5.00(s, 2 H), 4.43(m, 1 H), 4.39(s, 2 H), 2.28(s, 3 H), 2.09(s, 3 H), 1.21(s, 3 H), 1.19 (s, 3 H). MS calculated for C$_{31}$H$_{31}$FN$_5$O$_5$ (M + H$^+$) 572.2, found 572.3 |
| 38 | 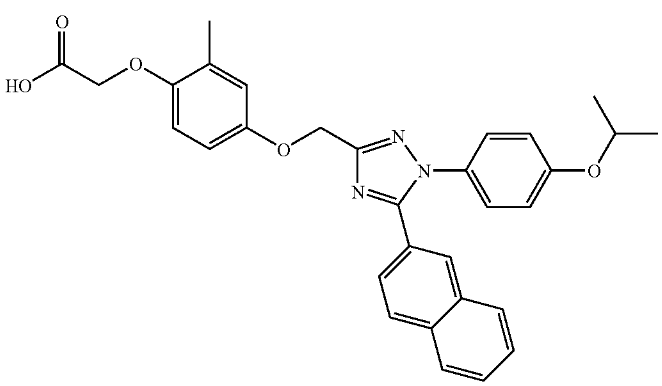 | $^1$H-NMR (400 MHz, CDCl$_3$) δ = 8.10(s, 1 H), 7.72(m, 3 H), 7.45(m, 3 H), 7.22(d, J = 8.8 Hz, 2 H), 6.87(d, J = 2.8 Hz, 1 H), 6.83(d, J = 8.4 Hz, 2 H), 6.75(dd, J = 2.8, 8.8 Hz, 1 H), 6.60(d, J = 8.8 Hz, 1 H), 5.16 (s, 2 H), 4.51(m, 3 H), 2.20(s, 3 H), 1.30(s, 3 H), 1.28(s, 3 H). MS calculated for C$_{31}$H$_{30}$N$_3$O$_5$ (M + H$^+$) 524.2, found 524.3 |

TABLE 1-continued

| Compound Number | Compound Structure | Physical Data $^1$H NMR 400 MHz (DMSO-d$_6$) and/or MS (m/z) |
|---|---|---|
| 39 | 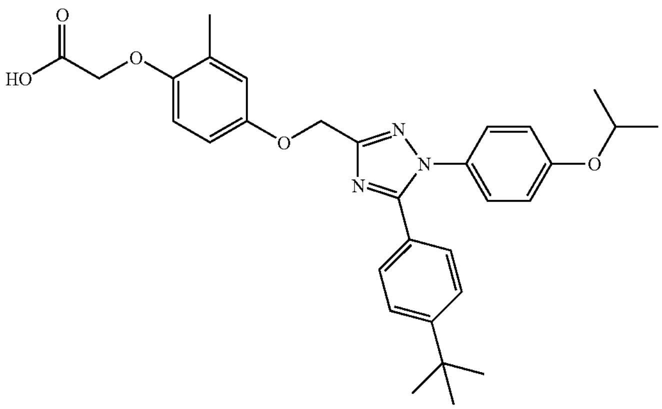 | $^1$H-NMR (400 MHz, CDCl$_3$) δ = 7.45(d, J = 8.4 Hz, 2 H), 7.35(d, J = 8.8 Hz, 2 H), 7.26 (d, J = 8.8 Hz, 2 H), 6.91(d, J = 8.8 Hz, 3 H), 6.77(dd, J = 2.8, 8.8 Hz, 1 H), 6.63(d, J = 8.8 Hz, 1 H), 5.19(s, 2 H), 4.59(m, 1 H), 4.56(s, 2 H), 2.26(s, 3 H), 1.36(s, 3 H), 1.34 (s, 3 H), 1.30(s, 9 H). MS calculated for C$_{31}$H$_{36}$N$_3$O$_5$ (M + H$^+$) 530.3, found 530.3 |
| 40 | 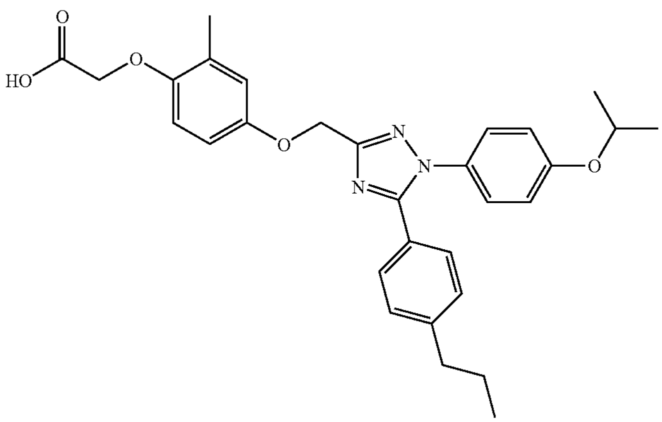 | $^1$H-NMR (400 MHz, CDCl$_3$) δ = 7.35(d, J = 8.4 Hz, 2 H), 7.17(d ,J = 8.8 Hz, 2 H), 7.07 (d, J = (d, J = 8.0 Hz, 2 H), 6.83(m, 3 H), 6.71(dd, J = 2.8, 8.8 Hz, 1 H), 6.57(d, J = 8.8 Hz, 1 H), 5.11(s, 2 H), 4.50(m, 1 H), 4.49(s, 2 H), 2.50(t, J = 7.16 Hz, 2 H), 2.18(s, 3 H), 1.55(m, 2 H), 1.29(s, 3 H), 1.27(s, 3 H), 0.85(t, J = 7.6 Hz, 3 H). MS calculated for C$_{30}$H$_{34}$N$_3$O$_5$ (M + H$^+$) 516.2, found 516.3 |
| 41 | 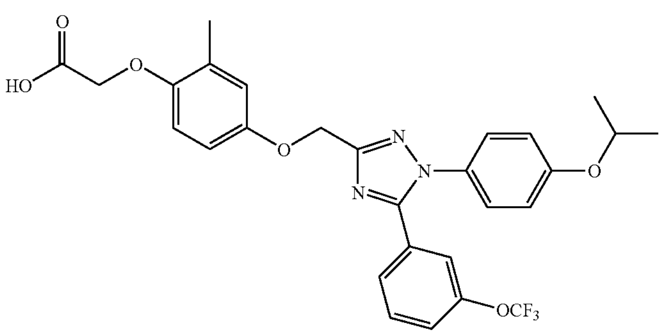 | $^1$H-NMR (400 MHz, CDCl$_3$) δ = 7.52(dt, J = 1.2, 8.0 Hz, 1 H), 7.41(t, J = 8.0 Hz, 1 H), 7.33(s, 1 H), 7.27(m, 1 H), 7.24(d, J = 8.4 Hz, 2 H), 6.93(m, 3 H), 6.79(dd, J = 2.8, 8.8 Hz, 1 H), 6.65(d, J = 8.8 Hz, 1 H), 5.18 (s, 2 H), 4.59(m, 1 H), 4.59(s, 2 H), 2.27(s, 3 H), 1.37(s, 3 H), 1.36(s, 3 H). MS calculated for C$_{28}$H$_{27}$F$_3$N$_3$O$_6$ (M + H$^+$) 558.2, found 558.2 |
| 42 | 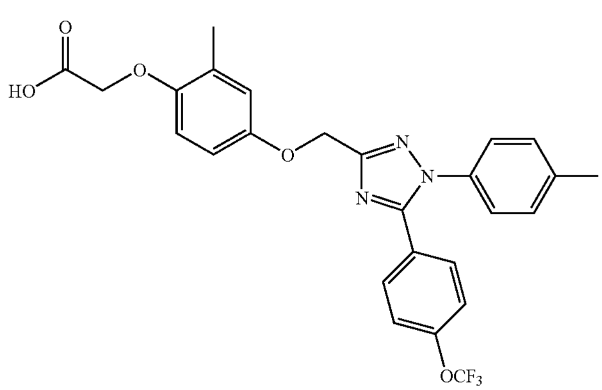 | $^1$H-NMR (400 MHz, CDCl$_3$) δ = 7.54(d, J = 8.8 Hz, 2 H), 7.23(m, 6 H), 6.90(d, J = 2.8 Hz, 1 H), 6.78(dd, J = 2.8, 8.8 Hz, 1 H), 6.65(d, J = 8.8 Hz, 1 H), 5.19(s, 2 H), 4.59 (s, 2 H), 2.42(s, 3 H), 2.26(s, 3 H). MS calculated for C$_{26}$H$_{23}$F$_3$N$_3$O$_5$ (M + H$^+$) 514.2, found 514.2 |

TABLE 1-continued

| Compound Number | Compound Structure | Physical Data $^1$H NMR 400 MHz (DMSO-$d_6$) and/or MS (m/z) |
|---|---|---|
| 43 | 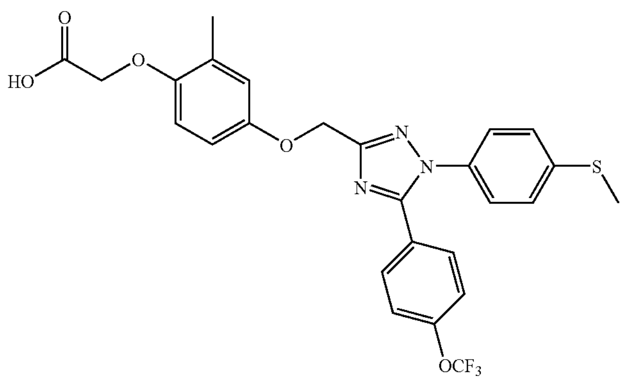 | $^1$H-NMR (400 MHz, CDCl$_3$) δ = 7.57(d, J = 8.8 Hz, 2 H), 7.27(m, 4 H), 7.20(d, J = 8.4 Hz, 2 H), 6.91(d, J = 2.0 Hz, 1 H), 6.79(dd, J = 2.4, 8.8 Hz, 1 H), 6.65(d, J = 8.8 Hz, 1 H), 5.17(s, 2 H), 4.58(s, 2 H), 2.52(s, 3 H), 2.27(s, 3 H). MS calculated for C$_{26}$H$_{23}$F$_3$N$_3$O$_5$S (M + H$^+$) 546.1, found 546.2 |
| 44 | 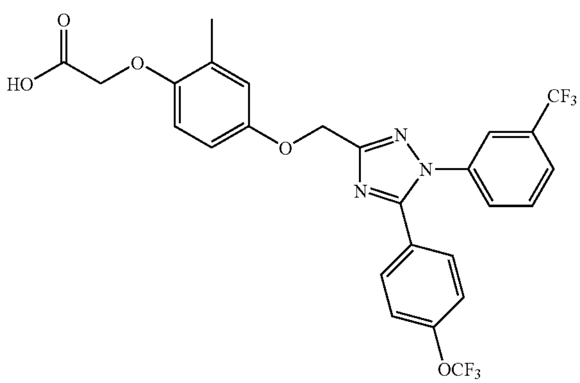 | $^1$H-NMR (400 MHz, CDCl$_3$) δ = 7.90(d, J = 8.8 Hz, 2 H), 7.73(m, 4 H), 7.42(d, J = 8.4 Hz, 2 H), 7.11(d, J = 2.0 Hz, 1 H), 7.02(dd, J = 2.4, 8.8 Hz, 1 H), 6.88(d, J = 8.4 Hz, 1 H), 5.37(s, 2 H), 4.80(s, 2 H), 2.46(s, 3 H). MS calculated for C$_{26}$H$_{20}$F$_6$N$_3$O$_5$ (M + H$^+$) 568.1, found 568.2 |

Transcriptional Assay

Transfection assays are used to assess the ability of compounds of the invention to modulate the transcriptional activity of the PPARs. Briefly, expression vectors for chimeric proteins containing the DNA binding domain of yeast GAL4 fused to the ligand-binding domain (LBD) of either PPARδ, PPARα or PPARγ are introduced via transient transfection into mammalian cells, together with a reporter plasmid where the luciferase gene is under the control of a GAL4 binding site. Upon exposure to a PPAR modulator, PPAR transcriptional activity varies, and this can be monitored by changes in luciferase levels. If transfected cells are exposed to a PPAR agonist, PPAR-dependent transcriptional activity increases and luciferase levels rise.

293T human embryonic kidney cells (8×10$^6$) are seeded in a 175 cm$^2$ flask a day prior to the start of the experiment in 10% FBS, 1% Penicillin/Streptomycin/Fungizome, DMEM Media. The cells are harvested by washing with PBS (30 ml) and then dissociating using trypsin (0.05%; 3 ml). The trypsin is inactivated by the addition of assay media (DMEM, CA-dextran fetal bovine serum (5%). The cells are spun down and resuspended to 170,000 cells/ml. A Transfection mixture of GAL4-PPAR LBD expression plasmid (1 μg), UAS-luciferase reporter plasmid (1 μg), Fugene (3:1 ratio; 6 μL) and serum-free media (200 μL) is prepared and incubated for 15-40 minutes at room temperature. Transfection mixtures are added to the cells to give 0.16 M cells/mL, and cells (50 μl/well) are then plated into 384 white, solid-bottom, TC-treated plates. The cells are further incubated at 37° C., 5.0% CO$_2$ for 5-7 hours. A 12-point series of dilutions (3 fold serial dilutions) are prepared for each test compound in DMSO with a starting compound concentration of 10 μM. Test compound (500 nl) is added to each well of cells in the assay plate and the cells are incubated at 37° C., 5.0% CO$_2$ for 18-24 hours. The cell lysis/luciferase assay buffer, Bright-Glo™ (25%; 25 μl; Promega), is added to each well. After a further incubation for 5 minutes at room temperature, the luciferase activity is measured.

Raw luminescence values are normalized by dividing them by the value of the DMSO control present on each plate. Normalized data is analyzed and dose-response curves are fitted using Prizm graph fitting program. EC50 is defined as the concentration at which the compound elicits a response that is halfway between the maximum and minimum values. Relative efficacy (or percent efficacy) is calculated by comparison of the response elicited by the compound with the maximum value obtained for a reference PPAR modulator.

Compounds of Formula I, in free form or in pharmaceutically acceptable salt form, exhibit valuable pharmacological properties, for example, as indicated by the in vitro tests described in this application.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound selected from Formulae Ia and Ic:

(Ia)

(Ic)

in which:
- m, n and p are independently selected from 0, 1, 2 and 3;
- each Y is independently selected from CH and N;
- $R_1$ is selected from XOXC(O)OR$_5$ and XC(O)OR$_5$; wherein X is selected from a bond and $C_{1-4}$alkylene; and $R_5$ is selected from hydrogen and $C_{1-6}$alkyl;
- $R_2$ is $C_{1-6}$alkyl;
- $R_3$ is selected from $C_{1-6}$alkoxy, $C_{1-6}$alkylthio, halo-substituted-$C_{1-6}$alkyl, halo-substituted-$C_{1-6}$alkoxy and halo-substituted-$C_{1-6}$alkylthio;
- $R_4$ is selected from $C_{1-6}$alkoxy, $C_{1-6}$alkylthio, halo-substituted-$C_{1-6}$alkyl, halo-substituted-$C_{1-6}$alkoxy, halo-substituted-$C_{1-6}$alkylthio and $C_{3-8}$heterocycloalkyl.

2. The compound of claim 1, in which:
- m, n and p are independently selected from 0, 1 and 2;
- Y is selected from CH and N;
- $R_1$ is XOXC(O)OR$_5$; wherein X is selected from a bond and $C_{1-4}$alkylene; and $R_5$ is selected from hydrogen and $C_{1-6}$alkyl;
- $R_2$ is selected from $C_{1-6}$alkyl;
- $R_3$ is selected from $C_{1-6}$alkoxy, halo-substituted-$C_{1-6}$alkyl and halo-substituted-$C_{1-6}$alkoxy; and
- $R_4$ is selected from $C_{1-6}$alkoxy, halo-substituted-$C_{1-6}$alkyl, halo-substituted-$C_{1-6}$alkoxy and $C_{3-8}$heterocycloalkyl.

3. The compound of claim 2 in which: m, n and p are 1; $R_1$ is —OCH$_2$C(O)OH; and $R_2$ is methyl.

4. The compound of claim 3 in which $R_3$ is selected from methoxy, trifluoromethoxy, trifluoromethyl and morpholino.

5. The compound of claim 4 in which $R_4$ is selected from trifluoromethyl, methoxy, isopropyloxy and trifluoromethoxy.

6. The compound of claim 5 selected from: {4-[2-(4-Methoxy-phenyl)-1-(4-trifluoromethyl-phenyl)-1H-imidazol-4-ylmethoxy]-2-methyl-phenoxy}-acetic acid; {4-[1-(6-Methoxy-pyridin-3-yl)-5-(4-trifluoromethoxy-phenyl)-1H-pyrazol-3-ylmethoxy]-2-methyl-phenoxy}-acetic acid; {4-[2-(4-Methoxy-phenyl)-1-(4-trifluoromethoxy-phenyl)-1H-imidazol-4-ylmethoxy]-2-methyl-phenoxy}-acetic acid; {4-[1-(4-Isopropoxy-phenyl)-2-(4-trifluoromethyl-phenyl)-1H-imidazol-4-ylmethoxy]-2-methyl-phenoxy}-acetic acid; {4-[1-(4-Methoxy-phenyl)-2-(4-trifluoromethyl-phenyl)-1H-imidazol-4-ylmethoxy]-2-methyl-phenoxy}-acetic acid; {2-Methyl-4-[1-(4-trifluoromethoxy-phenyl)-2-(4-trifluoromethyl-phenyl)-1H-imidazol-4-ylmethoxy]-phenoxy}-acetic acid; {4-[1-(6-Methoxy-pyridin-3-yl)-2-(4-trifluoromethyl-phenyl)-1H-imidazol-4-ylmethoxy]-2-methyl-phenoxy}-acetic acid; {4-[1-(4-Isopropoxy-phenyl)-2-(4-trifluoromethoxy-phenyl)-1H-imidazol-4-ylmethoxy]-2-methyl-phenoxy}-acetic acid; {4-[1-(4-Methoxy-phenyl)-2-(4-trifluoromethoxy-phenyl)-1H-imidazol-4-ylmethoxy]-2-methyl-phenoxy}-acetic acid; {4-[1,2-Bis-(4-trifluoromethoxy-phenyl)-1H-imidazol-4-ylmethoxy]-2-methyl-phenoxy}-acetic acid; {4-[1-(6-Methoxy-pyridin-3-yl)-2-(4-trifluoromethoxy-phenyl)-1H-imidazol-4-ylmethoxy]-2-methyl-phenoxy}-acetic acid; {4-[5-(4-Methoxy-phenyl)-1-(4-trifluoromethyl-phenyl)-1H-pyrazol-3-ylmethoxy]-2-methyl-phenoxy}-acetic acid; {4-[5-(4-Methoxy-phenyl)-1-(3-trifluoromethyl-phenyl)-1H-pyrazol-3-ylmethoxy]-2-methyl-phenoxy}-acetic acid; {4-[5-(4-Methoxy-phenyl)-1-(4-trifluoromethoxy-phenyl)-1H-pyrazol-3-ylmethoxy]-2-methyl-phenoxy}-acetic acid; {4-[1,5-Bis-(4-methoxy-phenyl)-1H-pyrazol-3-ylmethoxy]-2-methyl-phenoxy}-acetic acid; {2-Methyl-4-[5-(4-morpholin-4-yl-phenyl)-1-(4-trifluoromethyl-phenyl)-1H-pyrazol-3-ylmethoxy]-phenoxy}-acetic acid; {2-Methyl-4-[5-(4-morpholin-4-yl-phenyl)-1-(3-trifluoromethyl-phenyl)-1H-pyrazol-3-ylmethoxy]-phenoxy}-acetic acid; {2-Methyl-4-[5-(4-morpholin-4-yl-phenyl)-1-(4-trifluoromethoxy-phenyl)-1H-pyrazol-3-ylmethoxy]-phenoxy}-acetic acid; {4-[1-(4-Methoxy-phenyl)-5-(4-morpholin-4-yl-phenyl)-1H-pyrazol-3-ylmethoxy]-2-methyl-phenoxy}-acetic acid; {2-Methyl-4-[5-(3-trifluoromethoxy-phenyl)-1-(4-trifluoromethyl-phenyl)-1H-pyrazol-3-ylmethoxy]-phenoxy}-acetic acid; {2-Methyl-4-[5-(3-trifluoromethoxy-phenyl)-1-(3-trifluoromethyl-phenyl)-1H-pyrazol-3-ylmethoxy]-phenoxy}-acetic acid; {2-Methyl-4-[1-(4-trifluoromethoxy-phenyl)-5-(3-trifluoromethoxy-phenyl)-1H-pyrazol-3-ylmethoxy]-phenoxy}-acetic acid; {4-[1-(4-Methoxy-phenyl)-5-(3-trifluoromethoxy-phenyl)-1H-pyrazol-3-ylmethoxy]-2-methyl-phenoxy}-acetic acid; {4-[1,5-Bis-(4-trifluoromethoxy-phenyl)-1H-pyrazol-3-ylmethoxy]-2-methyl-phenoxy}-acetic acid; {4-[1-(4-Methoxy-phenyl)-5-(4-trifluoromethoxy-phenyl)-1H-pyrazol-3-ylmethoxy]-2-methyl-phenoxyl}-acetic acid; {2-Methyl-4-[1-(4-trifluoromethoxy-phenyl)-5-(4-trifluoromethyl-phenyl)-1H-pyrazol-3-ylmethoxy]-phenoxy}-acetic acid; and {4-[1-(4-Methoxy-phenyl)-5-(4-trifluoromethyl-phenyl)-1H-pyrazol-3-ylmethoxy]-2-methyl-phenoxy}-acetic acid.

7. A pharmaceutical composition comprising a therapeutically effective amount of a compound of claim 1 in combination with a pharmaceutically acceptable excipient.

8. A method for treating a disease or disorder in an animal in which modulation of PPAR activity can inhibit or ameliorate the pathology and/or symptomology of the disease, which method comprises administering to the animal a therapeutically effective amount of a compound of claim 1 where the disease or disorder is selected from the treatment of dyslipidemia, hyperlipidemia, hypercholesteremia, atherosclerosis, atherogenesis, hypertriglyceridemia, diabetes mellitus, Impaired Glucose Metabolism (IGM), Impaired Glucose Tolerance (IGT), and Syndrome X.

9. A pharmaceutical composition according to claim 7 for the treatment of dyslipidemia, hyperlipidemia, hypercholesteremia, atherosclerosis, hypertriglyceridemia, diabetes mellitus, Impaired Glucose Metabolism (IGM), Impaired Glucose Tolerance (IGT), and Syndrome-X.

* * * * *